(12) United States Patent
Vince et al.

(10) Patent No.: US 9,403,778 B2
(45) Date of Patent: Aug. 2, 2016

(54) AGENTS THAT PREVENT OR REPAIR SKIN DAMAGE

(71) Applicant: Regents of the University of Minnesota, Minneapolis, MN (US)

(72) Inventors: Robert Vince, Minneapolis, MN (US); Abbas Raza, Minneapolis, MN (US); Christine Dreis, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/371,900

(22) PCT Filed: Jan. 11, 2013

(86) PCT No.: PCT/US2013/021259
§ 371 (c)(1),
(2) Date: Jul. 11, 2014

(87) PCT Pub. No.: WO2013/106728
PCT Pub. Date: Jul. 18, 2013

(65) Prior Publication Data
US 2014/0350036 A1    Nov. 27, 2014

Related U.S. Application Data

(60) Provisional application No. 61/713,347, filed on Oct. 12, 2012, provisional application No. 61/586,548, filed on Jan. 13, 2012.

(51) Int. Cl.
| | | |
|---|---|---|
| *C07D 239/22* | (2006.01) |
| *C07D 487/04* | (2006.01) |
| *C07D 487/16* | (2006.01) |
| *C07D 403/12* | (2006.01) |
| *A61K 45/06* | (2006.01) |
| *A61K 31/506* | (2006.01) |
| *A61K 31/513* | (2006.01) |
| *A61K 31/519* | (2006.01) |
| *A61K 31/695* | (2006.01) |
| *A61K 8/49* | (2006.01) |
| *A61Q 17/04* | (2006.01) |
| *A61Q 19/00* | (2006.01) |

(52) U.S. Cl.
CPC ............ *C07D 239/22* (2013.01); *A61K 8/4953* (2013.01); *A61K 31/506* (2013.01); *A61K 31/513* (2013.01); *A61K 31/519* (2013.01); *A61K 31/695* (2013.01); *A61K 45/06* (2013.01); *A61Q 17/04* (2013.01); *A61Q 19/004* (2013.01); *C07D 403/12* (2013.01); *C07D 487/04* (2013.01); *C07D 487/16* (2013.01)

(58) Field of Classification Search
CPC ... C07D 239/22; C07D 487/04; C07D 487/16
USPC ............ 514/267, 274; 544/251, 296; 540/471
See application file for complete search history.

(56) References Cited

U.S. PATENT DOCUMENTS

| | | |
|---|---|---|
| 6,255,290 B1 | 7/2001 | von Borstel et al. |
| 6,465,440 B2 | 10/2002 | von Borstel et al. |
| 2004/0087614 A1 | 5/2004 | Baumann et al. |
| 2011/0158924 A1 | 6/2011 | Dickmann et al. |
| 2011/0171148 A1 | 7/2011 | Jones |

FOREIGN PATENT DOCUMENTS

WO    2006133876 A1    12/2006

OTHER PUBLICATIONS

Fenick et al., "Synthesis and Photochemical Cleavage of Cis-Syn Pyrimidine Cyclobutane Dimer Analogs", J. Org. Chem. 60, 624-631 (1995).
Golankiewicz et al., "Non-bonding Base-Base Interaction in Nucleic Acids. I. synthesis and Properties of Several 1,1'-Polimethylenebispyrimidines", Bulletin De L'Academie Polonaise De Sciences, vol. 18 (8), 449-454 (1970).
Golankiewicz et al., "Base-Base Interaction in Nucleic Acids. IX. The Effect of 3,3'Substituion on Solution-Phase Photodimerization and Base-Stacking Interaction of 1,1'-Trimethylenebis-5-Alkyluracils", Bulletin De L'Academie Polonaise Des Sciences, vol. 22 (11), 945-954 (1974).
Golankiewicz et al., "Base-Base Interactiion in Nucleic Acids. X. Further Investigation on the Influence of 3,3' and 5,5' Substitution on Solution Phase Photodimerization of 1,1'-Trimethylenebis (5-alkyl)Uracils", Bulletin De L'Academie Polonaise Des Sciences, vol. 24 (4), 285-290 (1976).
Golankiewicz et al., "Synthesis and Photochemical Properties of Quasimetacyclophanes Derived from 5-Alkyluracils", Polish Journal of Chemistry vol. 52, 1365-1373 (1978).
Hanson et al., "Sunscreen enhancement of UV-induced reactive oxygen species in the skin", Free Radic Biol Med 41 (8), 1205-1212 (2006).
Hartman et al., "A Possible Chain Reaction in Photosensitized Splitting of Pyrimidine Dimers by a Protonated, Oxidized Flavin", J. Org. Chem. 57, 2302-2306 (1992).

(Continued)

*Primary Examiner* — Raymond Henley, III
(74) *Attorney, Agent, or Firm* — Viksnins Harris & Padys PLLP

(57) ABSTRACT

The invention provides compounds of formula I: or a salt thereof as described herein. The invention also provides dermatological compositions comprising a compound of formula I or mixtures of one or more compounds of formula I, processes for preparing compounds of formula I, intermediates useful for preparing compounds of formula I and therapeutic methods for protecting skin or DNA from photodamage or repairing photodamaged skin or DNA.

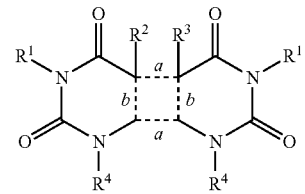

(I)

29 Claims, No Drawings

(56) References Cited

OTHER PUBLICATIONS

Itahara, "Preparation of Pyrimidinophanes from Pyrimidine Bases", Bull Chem Soc Jpn 69, 3239-3246 (1996).

Itahara, "NMR and UV Study of 1,1'-(α,ω-Alkanediyl)bis[thymine] and 1,1'-( α,ω-Alkanediyl)bis[uracil]", Bull. Chem. Soc. Jpn. 70, 2239-2247 (1997).

Kertsnus-Banchik et al., "Dinuclear Silicon Complexes of Uracil, Barbituric Acid, and 5,5-Dimethylbarbituric Acid: Hydrolytic Formation of Cyclic Oligomers", Organometallics 29, 5435-5445 (2010).

Knowland et al., "Sunlight-induced mutagenicity of a common sunscreen ingredient", FEBS Letters 324, 309-313 (1993).

Koroniak et al., "Effect of Polymethylene Chain Length on Photodimerization of 1,1'-Polymethylenebis(5-Alkyl)Uracils", Polish Journal of Chemistry, vol. 52, 1567-1568 (1978).

Koroniak et al., "Photosynthesis of Dimers Derived from 2,4-Diketopyrimidine Dependent on the Rigidity of the Molecule", Zeszyty Problemowe Postepów Nauk Rolniczych, vol. 271, 201-208 (1984). [English Translation of Summary.].

Lafay et al., "Synthesis of Novel C-Organiosilicon Derivatives, Potential Inhibitors of HIV Reverse Transcription", Phosphorus, Sulfur and Silicon, vol. 102, 155-168 (1995).

Langer, "Stacking and Hydrogen Bonding in N,N'-Polymethylenebis (5-Alkyl)Uracils in the Light of Laser Raman Spectroscopy Data", Journal of Molecular Structure 125, 109-116 (1984).

Leonard et al., "Solid State Ultraviolet Irradiation of 1,1'-Trimethylenebisthymine and Photosensitized Irradiation of 1,1'-Polymethylenebisthymines", Journal of American Chemical Society 95 (7), 2320-2324 (1973).

Leonard et al., "Stereochemically Controlled Photoreactions between Two Thymine Rings", Journal American Chemical Society 96 (18), 5904-5910 (1974).

Loser et al., "IL-10 controls ultraviolet-induced carcinogenesis in mice", J Imm 179, 365-371 (2007).

Lovett et al., "The Role of Michael Adducts in Pyrimidine Chemistry. Reactions of 3-(β-Methanesulfonyloxyethyl)-1-methyluracil with Bases", J. Org. Chem. vol. 40 (12), 1722-1728 (1975).

Mitchell et al., "Identification of a non-dividing subpopulation of mouse and human epidermal cells exhibiting high levels of persistent ultraviolet photodamage", J Invest Derm 117, 590-595 (2001).

Mosley et al., "Light-induced cytotoxicity and genotoxicity of a sunscreen agent, 2-phenylbenzimidazole in *Salmonella typhimurium* TA 102 and HaCaT keratinocytes", Int J Environ Res Public Health 4(2), 126-131 (2007).

Nguyen et al., "A Prebiotic Role for 8-Oxoguanosine as a Flavin Mimic in Pyrimidine Dimer Photorepair", J. Am. Chem. Soc. 133, 14586-14589 (2011).

Patent Cooperation Treaty, International Searching Authority, Search Report and Written Opinion for PCT/US2013/021259, 17 pages, Jun. 20, 2013.

Pouwels et al., "Photo-CIDNP Study of Pyrimidine Dimer Splitting I: Reactions Involving Pyrimidine Radical Cation Intermediates", Photochemistry and Photobiology vol. 61 (6), 563-574 (1995).

Semenov et al., "Antibacterial and antifungal activity of acyclic and macrocyclic uracil derivatives with quaternized nitrogen atoms in spacers", European Journal of Medicinal Chemistry 41, 1093-1101 (2006).

Semenov et al., "Copper(II) Bromide Complexes with Acyclic and Cyclic Pyrimidine-Containing Phane Ligands", Russian Journal of Coordination Chemistry, vol. 33 (9), 685-691 (2007).

Torizawa et al., "Investigation of the cyclobutane pyrimidine dimer (CPD) photolyase DNA recognition mechanism by NMR analyses", JBC 279, 32950-32956 (2004).

Vink, "Biological consequences of cyclobutane pyrimidine dimers", J Photochem Photobiol, 31, 101-104 (2001).

Zarnowski et al., "Base-Base Interaction in Nucleic Acids. VII. NMR Properties of 1,1'-Polymethylenebispyrimidine Derivatives with Bulky Substituents in 5,5'-Positions", Bulletin De L'Academie Polonaise Des Sciences, vol. 22 (2), 123-128 (1974).

AGENTS THAT PREVENT OR REPAIR SKIN DAMAGE

RELATED APPLICATIONS

This application is a 371 national stage application of PCT/US2013/021259 filed 11 Jan. 2013, which claims priority to U.S. Provisional Application No. 61/713,347, filed on 12 Oct. 2012, and claims priority to U.S. Provisional Application No. 61/586,548, filed on 13 Jan. 2012, all of which are incorporated by reference in their entirety.

BACKGROUND OF THE INVENTION

Skin cancer is the most common cancer diagnosed in the United States and the incidence of skin cancer continues to rise. Epidemiological studies have documented that extensive sun exposure increases the risk of developing non-melanoma skin cancer. Photoprotection is the primary preventative health strategy. Sunscreens are one of the most important forms of photoprotection.

In general, the active ingredients in commercial sunscreens are mostly aromatic hydrocarbons which absorb the light from ultraviolet radiation (UV) and degrade or generate very reactive intermediates via free radicals. Such break down products which can be potentially harmful to the skin (*Free Radical Biology & Medicine* 2006, 41, 1205-12). Several recent reports have suggested that current sunscreens may increase cancer risk (*Int J. Environ. Res. Public Health* 2007, 4(2), 126-31; *FEBS Letters* 1993, 324, 309-13).

Currently there is a need for agents or compositions comprising said agents that prevent or repair DNA damage in the skin or that prevent or repair photo-damage to the skin. There is also a need for agents or compostions that are useful as sunscreens. There is also a need for agents that act through unique mechanisms of action or that are effective at lower concentrations or that produce non-toxic photoproducts or less toxic photoproducts or lower concentrations of photoproducts.

SUMMARY OF THE INVENTION

The agents and compositions of the present invention have a unique mechanism of action compared to existing agents and compositions (e.g. sunscreens) in the market. The agents of the present invention absorb UV light and provide photoprotection to the skin. The resulting photo-products initiate the body's natural defense mechanisms by increasing cellular production of DNA repairing enzymes. Thus, the invention provides compounds and compositions that have dual action of providing photo-protection and stimulating repair processes.

In one embodiment, the invention provides a compound of the invention which is a compound of formula I:

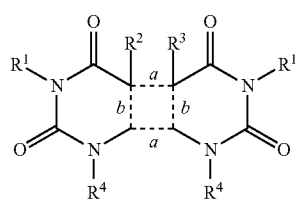

wherein:
each $R^1$ is independently H, $(C_1\text{-}C_6)$alkyl, $(C_3\text{-}C_7)$carbocycle or $R_aC(=O)$—, and the two $R^4$ groups together form a —$(C_3\text{-}C_8)$alkyl-group, a —$(C_2\text{-}C_6)$alkyl-Y—$(C_2\text{-}C_6)$alkyl-group or a —$(C_1\text{-}C_6)$alkyl-Y'—$(C_1\text{-}C_6)$alkyl-group; or each $R^4$ is independently H, $(C_1\text{-}C_6)$alkyl, $(C_3\text{-}C_7)$carbocycle or $R_aC(=O)$—, and the two $R^1$ groups together form a —$(C_3\text{-}C_8)$alkyl-group, a —$(C_2\text{-}C_6)$alkyl-Y—$(C_2\text{-}C_6)$alkyl-group or a —$(C_1\text{-}C_6)$alkyl-Y'—$(C_1\text{-}C_6)$alkyl-group; or the two $R^4$ groups together form a —$(C_3\text{-}C_8)$alkyl-group, a —$(C_2\text{-}C_6)$alkyl-Y—$(C_2\text{-}C_6)$alkyl group or a —$(C_1\text{-}C_6)$alkyl-Y'—$(C_1\text{-}C_6)$alkyl-group and the two $R^1$ groups together form a —$(C_3\text{-}C_8)$alkyl-group, a —$(C_2\text{-}C_6)$alkyl-Y—$(C_2\text{-}C_6)$alkyl-group or a —$(C_1\text{-}C_6)$alkyl-Y'—$(C_1\text{-}C_6)$alkyl-group;

the dashed bonds labeled "a" are absent and the dashed bonds labeled "b" are double bonds; or all the dashed bonds are single bonds;

$R^2$ is H, $(C_1\text{-}C_6)$alkyl or aryl, wherein aryl is optionally substituted with one or more $Z^1$ groups;

$R^3$ is H, $(C_1\text{-}C_6)$alkyl or aryl, wherein aryl is optionally substituted with one or more $Z^1$ groups;

Y is O, S, NH, $NR_c$, P, P(=O) or POH;

Y' is $Si(R_b)_2$ or —$Si(R_b)_2$—O—$Si(R_b)_2$—;

each $R_a$ is independently $(C_1\text{-}C_6)$alkyl, $(C_3\text{-}C_7)$carbocycle or aryl, wherein aryl is optionally substituted with one or more $Z^1$ groups;

each $R_b$ is independently $(C_1\text{-}C_6)$alkyl, $(C_3\text{-}C_7)$carbocycle or aryl, wherein aryl is optionally substituted with one or more $Z^1$ groups;

each $R_c$ is independently $R_g$ or a $C_1\text{-}C_{18}$ saturated or unsaturated carbon chain that is optionally substituted with one or more groups independently selected from oxo (=O), hydroxy, mercapto, $(C_1\text{-}C_6)$alkoxy, $(C_1\text{-}C_6)$alkoxycarbonyl, $(C_1\text{-}C_6)$alkanoyloxy, $NR_dR_e$, carboxy, and aryl, wherein any aryl of $R_c$ is optionally substituted with one or more $R_f$;

each $R_d$ and $R_e$ is independently selected from H, $(C_1\text{-}C_6)$alkyl, $(C_1\text{-}C_6)$alkanoyl, phenyl, benzyl, and $R_g$;

each $R_f$ is independently selected from $(C_1\text{-}C_6)$alkyl, $(C_1\text{-}C_6)$alkoxy, $(C_1\text{-}C_6)$alkoxycarbonyl, $(C_1\text{-}C_6)$alkanoyloxy, —C(=O)-phenyl, and —C(=O)$CH_2C$(=O)-phenyl, wherein any phenyl is optionally substituted with one or more groups independently selected from $(C_1\text{-}C_6)$alkyl, —$SO_3H$, and $(C_1\text{-}C_6)$alkoxy;

each $R_g$ is

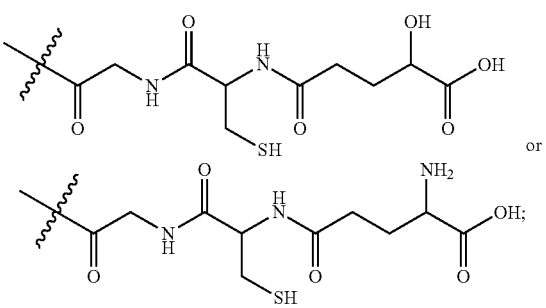

each $Z^1$ is independently selected from $(C_1\text{-}C_6)$alkyl, halogen, —CN, —$OR_{n1}$, —$NR_{q1}R_{r1}$, —$NR_{n1}COR_{p1}$, —$NR_{n1}CO_2R_{p1}$, $NO_2$, —C(O)$R_{n1}$, —C(O)$OR_{n1}$ and —C(O)$NR_{q1}R_{r1}$, wherein any $(C_1\text{-}C_6)$alkyl of $Z^1$ is optionally substituted with one or more (e.g. 1, 2, 3, 4, 5 or 6) halogen;

each $R_{n1}$ is independently selected from H and $(C_1\text{-}C_6)$alkyl, wherein any $(C_1\text{-}C_6)$alkyl of $R_{n1}$ is optionally substituted with one or more (e.g. 1, 2, 3, 4, 5 or 6) halogen;

each $R_{p1}$ is independently $(C_1\text{-}C_6)$alkyl; and $R_{q1}$ and $R_{r1}$ are each independently selected from H and $(C_1-C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine;

or a salt thereof.

The invention also provides a composition comprising a compound of formula I or a pharmaceutically acceptable salt thereof, and a pharmaceutically acceptable carrier.

The invention also provides a composition comprising a mixture of two or more compounds of formula I, or pharmaceutically acceptable salts thereof, and a pharmaceutically acceptable carrier.

The invention also provides a method for protecting mammal (e.g. human) skin from photo-damage comprising contacting the skin with one or more compounds of formula I or pharmaceutically acceptable salts thereof.

The invention also provides a method for protecting DNA in mammal (e.g. human) skin from photo-damage comprising contacting the skin with one or more compounds of formula I or pharmaceutically acceptable salts thereof.

The invention also provides a method for repairing photo-damage in mammal (e.g. human) skin comprising contacting the skin with one or more compounds of formula I or pharmaceutically acceptable salts thereof.

The invention also provides a method for stimulating DNA repair in mammal (e.g. human) skin comprising contacting the skin with one or more compounds of formula I or pharmaceutically acceptable salts thereof.

The invention also provides a method for preventing skin cancer (e.g. basal cell carcinoma or squamous cell carcinoma) in a mammal (e.g. a human) or reducing the likelihood of contracting skin cancer (e.g. basal cell carcinoma or squamous cell carcinoma) in a mammal (e.g. a human) comprising contacting the skin with one or more compounds of formula I or pharmaceutically acceptable salts thereof.

The invention also provides a method for reversing the signs of skin aging or preventing skin wrinkles in a mammal (e.g. a human) comprising contacting the skin with one or more compounds of formula I or pharmaceutically acceptable salts thereof.

The invention also provides a method for treating xeroderma pigmentosum in a mammal (e.g. a human) comprising contacting the skin with one or more compounds of formula I or pharmaceutically acceptable salts thereof.

The invention also provides a method for treating or preventing ionizing radiation damage in a mammal (e.g. a human) comprising treating the mammal with one or more compounds of formula I or pharmaceutically acceptable salts thereof.

The invention also provides the use of one or more compounds of formula I or pharmaceutically acceptable salts thereof, for the manufacture of a medicament useful for protecting mammal skin from photo-damage.

The invention also provides the use of one or more compounds of formula I or pharmaceutically acceptable salts thereof, for the manufacture of a medicament useful for protecting DNA in mammal skin from photo-damage.

The invention also provides the use of one or more compounds of formula I or pharmaceutically acceptable salts thereof, for the manufacture of a medicament useful for repairing photo-damage in mammal skin.

The invention also provides the use of one or more compounds of formula I or pharmaceutically acceptable salts thereof, for the manufacture of a medicament useful for stimulating DNA repair in mammal skin.

The invention also provides the use of one or more compounds of formula I or pharmaceutically acceptable salts thereof, for the manufacture of a medicament useful for preventing skin cancer (e.g. basal cell carcinoma or squamous cell carcinoma) or reducing the likelihood of developing skin cancer (e.g. basal cell carcinoma or squamous cell carcinoma) in a mammal.

The invention also provides the use of one or more compounds of formula I or pharmaceutically acceptable salts thereof, for the manufacture of a medicament useful for reversing the signs of skin aging or preventing skin wrinkles in a mammal.

The invention also provides the use of one or more compounds of formula I or pharmaceutically acceptable salts thereof, for the manufacture of a medicament useful for treating xeroderma pigmentosum in a mammal.

The invention also provides the use of one or more compounds of formula I or pharmaceutically acceptable salts thereof, for the manufacture of a medicament useful for treating or preventing ionizing radiation damage in a mammal.

The invention also provides processes and intermediates disclosed herein that are useful for preparing compounds of formula I or salts thereof.

DETAILED DESCRIPTION

The following definitions are used, unless otherwise described.

The term "alkyl" as used herein refers to straight and branched hydrocarbon groups. Reference to an individual radical such as propyl embraces only the straight chain radical, a branched chain isomer such as isopropyl being specifically referred to.

The term "halo" or "halogen" as used herein refers to fluoro, chloro, bromo and iodo.

The term "carbocycle" or "carbocyclyl" refers to a single saturated (i.e., cycloalkyl) or a single partially unsaturated (e.g., cycloalkenyl, cycloalkadienyl, etc.) ring having 3 to 7 carbon atoms (i.e. $(C_3-C_7)$carbocycle). The term "carbocycle" or "carbocyclyl" also includes multiple condensed ring systems (e.g. ring systems comprising 2, 3 or 4 carbocyclic rings). Accordingly, carbocycle includes multicyclic carbocycles having 7 to 12 carbon atoms as a bicycle, and up to about 20 carbon atoms as a polycycle. Multicyclic carbocycles can be connected to each other via a single carbon atom to form a spiro connection (e.g. spiropentane, spiro[4,5]decane, spiro[4.5]decane, etc), via two adjacent carbon atoms to form a fused connection such as a bicyclo[4,5], [5,5], [5,6] or [6,6] system, or 9 or 10 ring atoms arranged as a bicyclo[5,6] or [6,6] system (e.g. decahydronaphthalene, norsabinane, norcarane) or via two non-adjacent carbon atoms to form a bridged connection (e.g. norbornane, bicyclo [2.2.2]octane, etc). The "carbocycle" or "carbocyclyl" may also be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl and cycloheptyl.

The term "aryl" as used herein refers to a single aromatic ring or a multiple condensed ring system. For example, an aryl group can have 6 to 20 carbon atoms, 6 to 14 carbon atoms, or 6 to 12 carbon atoms. Aryl includes a phenyl radical. Aryl also includes multiple condensed ring systems (e.g. ring systems comprising 2, 3 or 4 rings) having about 9 to 20 carbon atoms in which at least one ring is aromatic. Such multiple condensed ring systems may be optionally substituted with one or more (e.g. 1, 2 or 3) oxo groups on any carbocycle portion of the multiple condensed ring system. It is to be understood that the point of attachment of a multiple condensed ring system, as defined above, can be at any position of the ring system including an aryl or a carbocycle portion of the ring. Typical aryl groups include, but are not limited to, phenyl, indenyl, naphthyl, 1,2,3,4-tetrahydronaphthyl, anthracenyl, and the like.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

Specific values listed below for radicals, substituents, and ranges, are for illustration only; they do not exclude other defined values or other values within defined ranges for the radicals and substituents. Specific values listed are values for compounds of formula I and II as well as all sub-formulas of formula I (e.g. formulas Ia, Ib Ic, Id, Ie, If etc.).

A specific group of compounds of formula I are compounds of formula Ia:

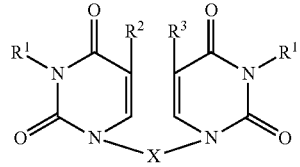

Ia wherein X is a —($C_3$-$C_8$)alkyl-group or a —($C_2$-$C_6$)alkyl-Y—($C_2$-$C_6$)alkyl-group or a —($C_1$-$C_6$)alkyl-Y'—($C_1$-$C_6$)alkyl-group; or a salt thereof Another specific group of compounds of formula I are compounds of formula Ib:

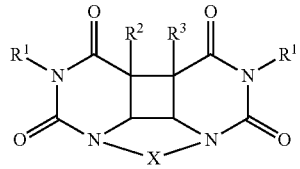

Ib wherein X is a —($C_3$-$C_8$)alkyl-group or a —($C_2$-$C_6$)alkyl-Y—($C_2$-$C_6$)alkyl-group or a —($C_1$-$C_6$)alkyl-Y'—($C_1$-$C_6$)alkyl-group; or a salt thereof.

Another specific group of compounds of formula I are compounds of formula Ic:

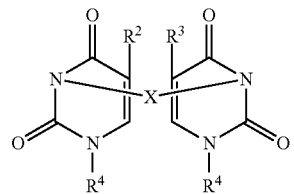

Ic wherein X is a —($C_3$-$C_8$)alkyl-group or a —($C_2$-$C_6$)alkyl-Y—($C_2$-$C_6$)alkyl-group or a —($C_1$-$C_6$)alkyl-Y'—($C_1$-$C_6$)alkyl-group; or a salt thereof.

Another specific group of compounds of formula I are compounds of formula Id:

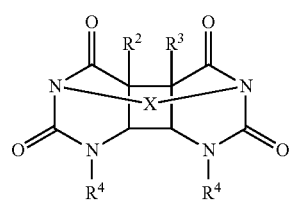

Id wherein X is a —($C_3$-$C_8$)alkyl-group or a —($C_2$-$C_6$)alkyl-Y—($C_2$-$C_6$)alkyl-group or a —($C_1$-$C_6$)alkyl-Y'—($C_1$-$C_6$)alkyl-group; or a salt thereof.

Another specific group of compounds of formula I are compounds of formula Ie:

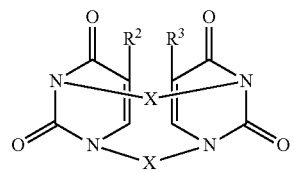

Ie wherein each X is independently a —($C_3$-$C_8$)alkyl-group or a —($C_2$-$C_6$)alkyl-Y—($C_2$-$C_6$)alkyl-group or a —($C_1$-$C_6$)alkyl-Y'—($C_1$-$C_6$)alkyl-group; or a salt thereof.

Another specific group of compounds of formula I are compounds of formula If:

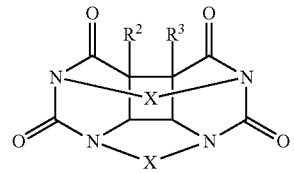

If wherein each X is independently a —($C_3$-$C_8$)alkyl-group or a —($C_2$-$C_6$)alkyl-Y—($C_2$-$C_6$)alkyl-group or a —($C_1$-$C_6$)alkyl-Y'—($C_1$-$C_6$)alkyl-group; or a salt thereof.

Specifically, ($C_1$-$C_6$)alkyl can be methyl, ethyl, propyl, isopropyl, butyl, iso-butyl, sec-butyl, pentyl, 3-pentyl or hexyl.

Specifically, $(C_3-C_7)$carbocycle can be cyclopropyl, cyclobutyl, cyclopentyl, cyclohexyl, cycloheptyl and partially unsaturated derivatives thereof.

A specific value for $R^1$ is H.

A specific value for X is $—(C_3-C_8)$alkyl- or $—(C_2-C_6)$alkylY$(C_2-C_6)$alkyl-.

Another specific value for X is $—(C_2-C_6)$alkylY$(C_2-C_6)$alkyl-.

A specific group of compounds of formula I are compounds wherein each $R^1$ is independently H or $(C_1-C_6)$alkyl, and the two $R^4$ groups together form a $—(C_2-C_6)$alkyl-Y—$(C_2-C_6)$alkyl-group.

A specific group of compounds of formula I are compounds wherein $R^1$ is H and X is $—(C_2-C_6)$alkyl-Y—$(C_2-C_6)$alkyl-; or $R^1$ is $(C_1-C_6)$alkyl, $(C_3-C_7)$carbocycle, aryl or $R_aC(=O)$—; and X is $—(C_3-C_8)$alkyl- or $—(C_2-C_6)$alkyl-Y—$(C_2-C_6)$alkyl.

A specific value for Y is NH.

A specific group of compounds of formula I are compounds wherein $R^2$ and $R^3$ are each independently $(C_1-C_6)$alkyl.

A specific group of compounds of formula I are compounds wherein $R^2$ and $R^3$ are each methyl.

A specific compound of formula I is:

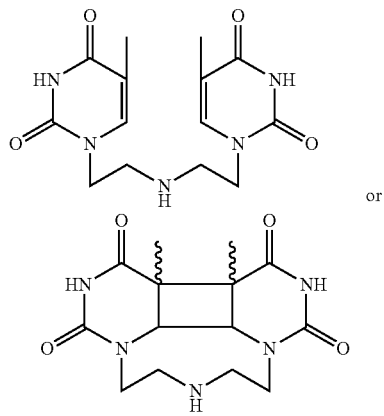

or a salt thereof.

In one embodiment of the invention the compounds of formula I do not include:

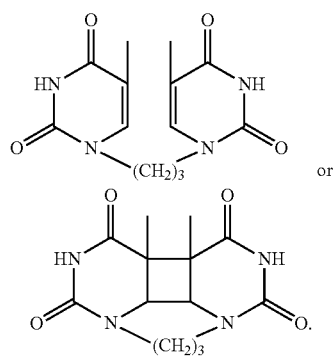

In another embodiment of the invention the compounds of formula I do not include:

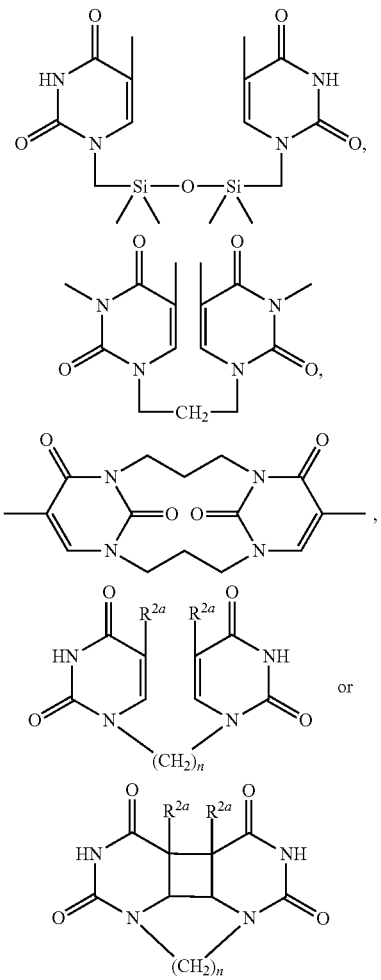

wherein each $R^{2a}$ is methyl or each $R^{2a}$ is ethyl; and n is 3-6.

A specific group of compounds are compounds of formula I wherein:

each $R^1$ is independently H, $(C_1-C_6)$alkyl, $(C_3-C_7)$carbocycle or $R_aC(=O)$—, and the two $R^4$ groups together form a $—(C_3-C_8)$alkyl-group, a $—(C_2-C_6)$alkyl-Y—$(C_2-C_6)$alkyl-group or a $—(C_1-C_6)$alkyl-Y'—$(C_1-C_6)$alkyl-group; or each $R^4$ is independently H, $(C_1-C_6)$alkyl, $(C_3-C_7)$carbocycle or $R_aC(=O)$—, and the two $R^1$ groups together form a $—(C_3-C_8)$alkyl-group, a $—(C_2-C_6)$alkyl-Y—$(C_2-C_6)$alkyl-group or a $—(C_1-C_6)$alkyl-Y'—$(C_1-C_6)$alkyl-group; or the two $R^4$ groups together form a $—(C_3-C_8)$alkyl-group, a $—(C_2-C_6)$alkyl-Y—$(C_2-C_6)$alkyl group or a $—(C_1-C_6)$alkyl-Y'—$(C_1-C_6)$alkyl-group and the two $R^1$ groups together form a $—(C_3-C_8)$alkyl-group, a $—(C_2-C_6)$alkyl-Y—$(C_2-C_6)$alkyl-group or a $—(C_1-C_6)$alkyl-Y'—$(C_1-C_6)$alkyl-group;

the dashed bonds labeled "a" are absent and the dashed bonds labeled "b" are double bonds; or all the dashed bonds are single bonds;

$R^2$ is H, $(C_1-C_6)$alkyl or aryl, wherein aryl is optionally substituted with one or more (e.g. 1, 2, 3, 4 or 5) $Z^1$ groups;

$R^3$ is H, $(C_1-C_6)$alkyl or aryl, wherein aryl is optionally substituted with one or more (e.g. 1, 2, 3, 4 or 5) $Z^1$ groups;

Y is O, S, NH, P, P(=O) or POH;

Y' is Si(R_b)_2 or —Si(R_b)_2—O—Si(R_b)_2—;

each $R_a$ is independently $(C_1-C_6)$alkyl, $(C_3-C_7)$carbocycle or aryl, wherein aryl is optionally substituted with one or more (e.g. 1, 2, 3, 4 or 5) $Z^1$ groups;

each $R_b$ is independently $(C_1-C_6)$alkyl, $(C_3-C_7)$carbocycle or aryl, wherein aryl is optionally substituted with one or more (e.g. 1, 2, 3, 4 or 5) $Z^1$ groups; and each $Z^1$ is independently selected from $(C_1-C_6)$alkyl, halogen, —CN, —OR_{n1}, —NR_{q1}R_{r1}, —NR_{n1}COR_{p1}, —NR_{n1}CO_2R_{p1}, NO_2, —C(O)R_{n1}, —C(O)OR_{n1} and —C(O)NR_{q1}R_{r1}, wherein any $(C_1-C_6)$alkyl of $Z^1$ is optionally substituted with one or more (e.g. 1, 2, 3, 4, 5 or 6) halogen;

each $R_{n1}$ is independently selected from H and $(C_1-C_6)$alkyl, wherein any $(C_1-C_6)$alkyl of $R_{n1}$ is optionally substituted with one or more (e.g. 1, 2, 3, 4, 5 or 6) halogen;

each $R_{p1}$ is independently $(C_1-C_6)$alkyl; and $R_{q1}$ and $R_{r1}$ are each independently selected from H and $(C_1-C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine;

and salts thereof.

A specific compound is a compound selected from:

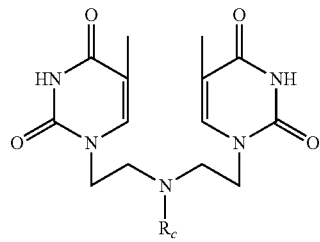

and

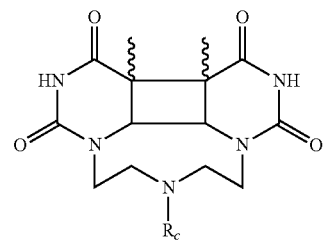

and salts thereof.

A specific $R_c$ is selected from butanoyl, hexadecanoyl, octadecanoyl, benzoyl, 3-phenylprop-2-enoyl, 3-(4-methoxyphenyl)prop-2-enoyl, 3-carboxy-3-hydroxypropanoyl, 2-(N-acetylamino)-3-mercaptopropanoyl, 4-(4-methoxy-3-sulfobenzoyl)benzoyl, 4-(3-(4-methoxyphenyl)-1,3-dioxopropyl)benzoyl, and

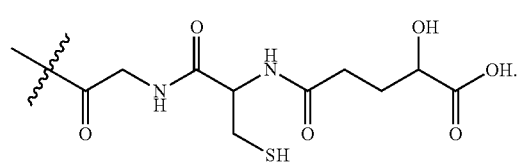 [SMILES: *C(=O)CNC(=O)C(CS)NC(=O)CCC(O)C(=O)O]

A specific compound is a compound selected from:

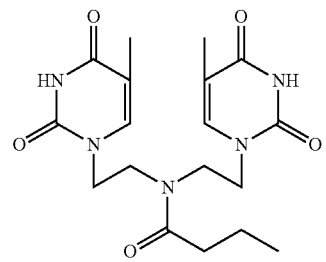

24a

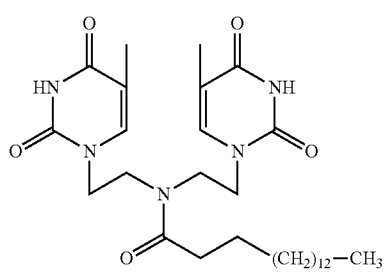

24b

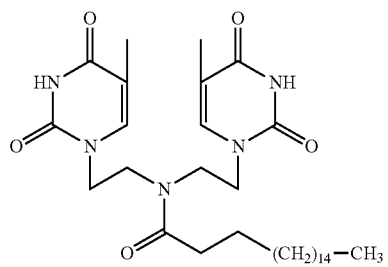

24c

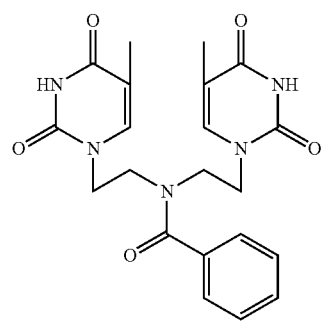

24d

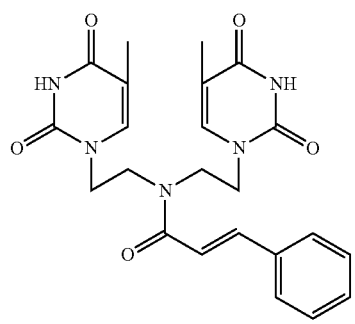

24e

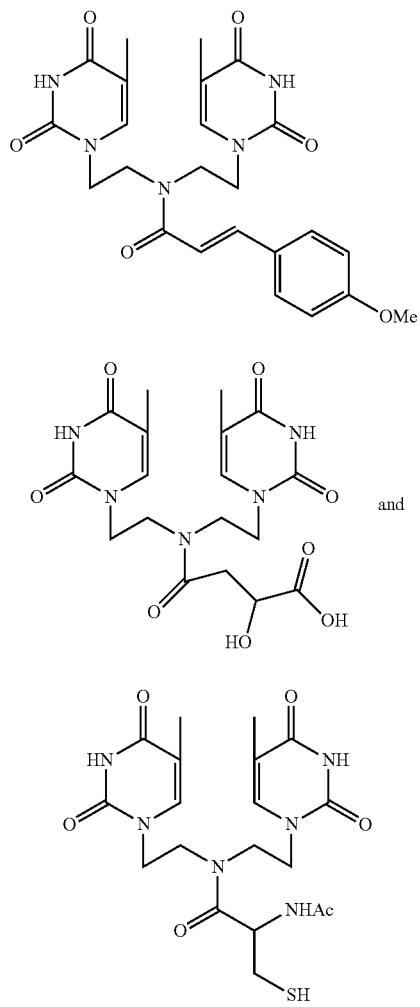
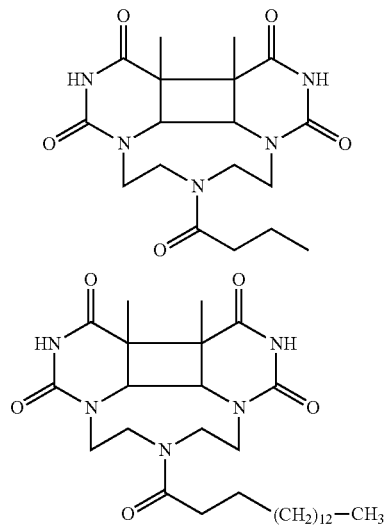
and salts thereof.
A specific compound is a compound selected from:
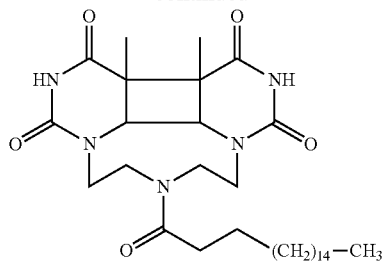
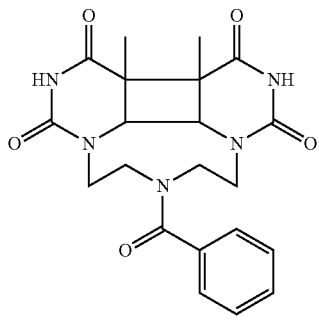
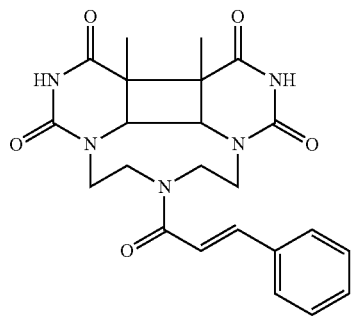
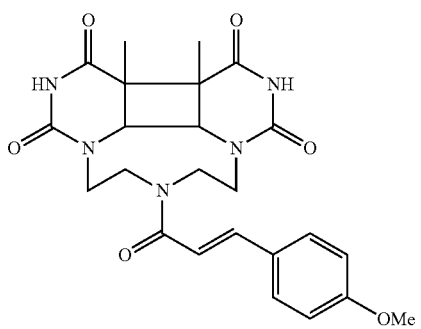
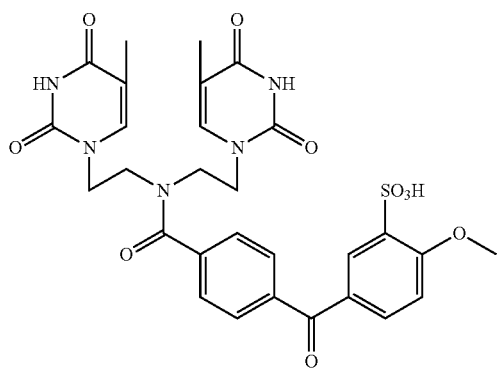

-continued

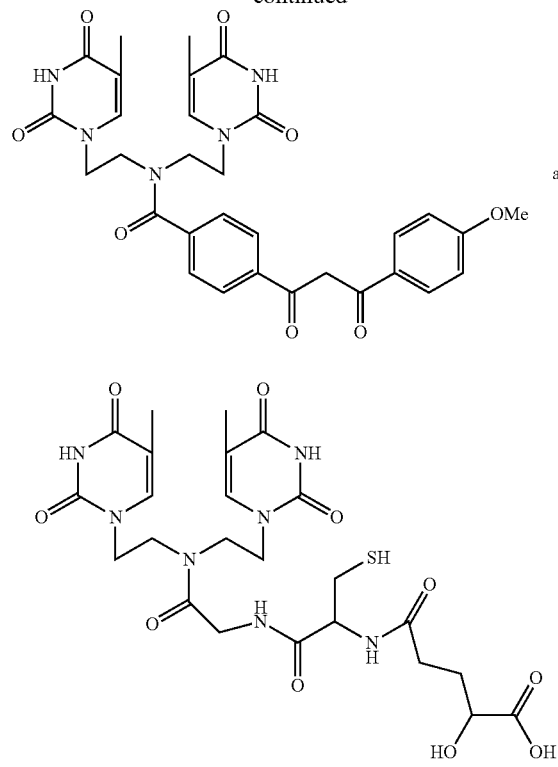

and salts thereof.

Processes for preparing compounds of formula I and formula II are provided as further embodiments of the invention and are illustrated in Schemes 1 and 2.

Scheme 1

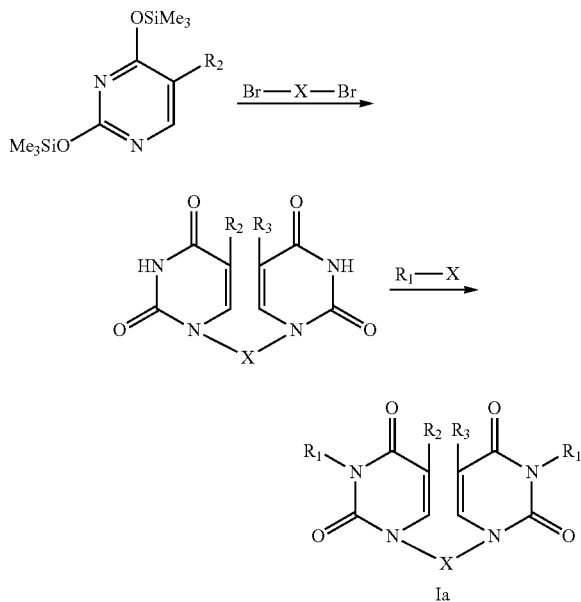

wherein X is —$(C_3-C_8)$alkyl- or —$(C_2-C_6)$alkyl-Y—$(C_2-C_6)$alkyl- or a —$(C_1-C_6)$alkyl-Y'—$(C_1-C_6)$alkyl-group and all other variables have the values as described herein.

Scheme 2

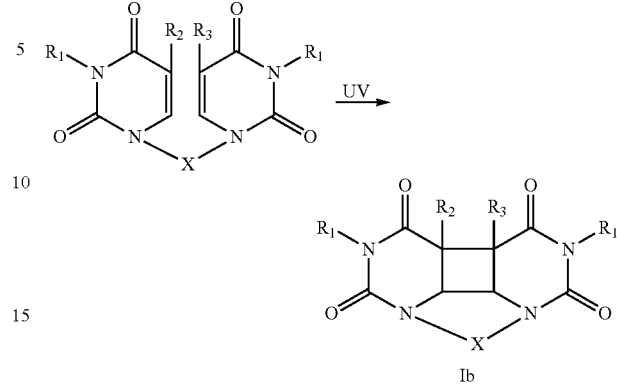

wherein X is —$(C_3-C_8)$alkyl- or —$(C_2-C_6)$alkyl-Y—$(C_2-C_6)$alkyl- or a —$(C_1-C_6)$alkyl-Y'—$(C_1-C_6)$alkyl-group and all other variables have the values as described herein.

Compounds of formula II can also stimulate DNA repair enzymes and thus have utility as described herein.

Accordingly, the invention also provides a composition comprising a compound of formula II:

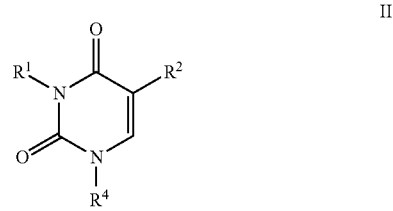

II or a pharmaceutically acceptable salt thereof, and a pharmaceutically acceptable carrier, wherein:

$R^1$ is H, $(C_1-C_6)$alkyl, $(C_3-C_7)$carbocycle or $R_aC(=O)$—;

$R^2$ is H, $(C_1-C_6)$alkyl or aryl, wherein aryl is optionally substituted with one or more (e.g. 1, 2, 3, 4 or 5) $Z^1$ groups;

$R^4$ is H, $(C_3-C_7)$carbocycle or $R_aC(=O)$—;

$R_a$ is or $(C_1-C_6)$alkyl, $(C_3-C_7)$carbocycle or aryl, wherein aryl is optionally substituted with one or more (e.g. 1, 2, 3, 4 or 5) $Z^1$ groups;

each $Z^1$ is independently selected from $(C_1-C_6)$alkyl, halogen, —CN, —$OR_{n1}$, —$NR_{q1}R_{r1}$, —$NR_{n1}COR_{p1}$, —$NR_{n1}CO_2R_{p1}$, $NO_2$, —$C(O)R_{n1}$, —$C(O)OR_{n1}$ and —$C(O)NR_{q1}R_{r1}$, wherein any $(C_1-C_6)$alkyl of $Z^1$ is optionally substituted with one or more (e.g. 1, 2, 3, 4, 5 or 6) halogen;

each $R_{n1}$ is independently selected from H and $(C_1-C_6)$alkyl, wherein any $(C_1-C_6)$alkyl of $R_{n1}$ is optionally substituted with one or more (e.g. 1, 2, 3, 4, 5 or 6) halogen;

each $R_{p1}$ is independently $(C_1-C_6)$alkyl; and $R_{q1}$ and $R_{r1}$ are each independently selected from H and $(C_1-C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine.

The invention also provides a composition comprising a mixture of two or more compounds of formula I or formula II (as described above), or pharmaceutically acceptable salts thereof, and a pharmaceutically acceptable carrier.

The invention also provides a method for protecting mammal (e.g. human) skin from photo-damage comprising contacting the skin with a compound of formula II or a pharmaceutically acceptable salt thereof.

The invention also provides a method for protecting DNA in mammal (e.g. human) skin from photo-damage comprising contacting the skin with a compound of formula II or a pharmaceutically acceptable salt thereof.

The invention also provides a method for repairing photo-damage in mammal (e.g. human) skin comprising contacting the skin with a compound of formula II or a pharmaceutically acceptable salt thereof.

The invention also provides a method for stimulating DNA repair in mammal (e.g. human) skin comprising contacting the skin with a compound of formula II or a pharmaceutically acceptable salt thereof.

The invention also provides a method for preventing skin cancer (e.g. basal cell carcinoma or squamous cell carcinoma) in a mammal (e.g. a human) or reducing the likelihood of contracting skin cancer (e.g. basal cell carcinoma or squamous cell carcinoma) in a mammal (e.g. a human) comprising contacting the skin with a compound of formula II or a pharmaceutically acceptable salt thereof.

The invention also provides a method for reversing the signs of skin aging or preventing skin wrinkles in a mammal (e.g. a human) comprising contacting the skin with a compound of formula II or a pharmaceutically acceptable salt thereof.

The invention also provides a method for treating xeroderma pigmentosum in a mammal (e.g. a human) comprising contacting the skin with a compound of formula II or a pharmaceutically acceptable salt thereof.

The invention also provides a method for treating or preventing ionizing radiation damage in a mammal (e.g. a human) comprising treating the mammal with a compound of formula II or a pharmaceutically acceptable salt thereof.

The invention also provides the use of a compound of formula II or a pharmaceutically acceptable salt thereof, for the manufacture of a medicament useful for protecting mammal skin from photo-damage.

The invention also provides the use of a compound of formula II or a pharmaceutically acceptable salt thereof, for the manufacture of a medicament useful for protecting DNA in mammal skin from photo-damage.

The invention also provides the use of a compound of formula II or a pharmaceutically acceptable salt thereof, for the manufacture of a medicament useful for repairing photo-damage in mammal skin.

The invention also provides the use of a compound of formula II or a pharmaceutically acceptable salt thereof, for the manufacture of a medicament useful for stimulating DNA repair in mammal skin.

The invention also provides the use of a compound of formula II or a pharmaceutically acceptable salt thereof, for the manufacture of a medicament useful for preventing skin cancer (e.g. basal cell carcinoma or squamous cell carcinoma) or reducing the likelihood of developing skin cancer (e.g. basal cell carcinoma or squamous cell carcinoma) in a mammal.

The invention also provides the use of a compound of formula II or a pharmaceutically acceptable salt thereof, for the manufacture of a medicament useful for reversing the signs of skin aging or preventing skin wrinkles in a mammal.

The invention also provides the use of a compound of formula II or a pharmaceutically acceptable salt thereof, for the manufacture of a medicament useful for treating xeroderma pigmentosum in a mammal.

The invention also provides the use of a compound of formula II or a pharmaceutically acceptable salt thereof, for the manufacture of a medicament useful for treating or preventing ionizing radiation damage in a mammal.

The invention also provides processes and intermediates disclosed herein that are useful for preparing compounds of formula II (as described above) or salts thereof.

In cases where compounds are sufficiently basic or acidic, a salt of a compound of the formula can be useful as an intermediate for isolating or purifying a compound of formula I or formula II. Additionally, administration of a compound of formula I or formula II as a pharmaceutically or dermatologically acceptable acid or base salt may be appropriate. Examples of pharmaceutically acceptable salts including dermatologically acceptable salts are organic acid addition salts formed with acids which form a physiological acceptable anion, for example, tosylate, methanesulfonate, acetate, citrate, malonate, tartrate, succinate, benzoate, ascorbate, $\alpha$-ketoglutarate, and $\alpha$-glycerophosphate. Suitable inorganic salts may also be formed, including hydrochloride, sulfate, nitrate, bicarbonate, and carbonate salts.

Pharmaceutically acceptable salts which include dermatologically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I or formula II can be formulated as pharmaceutical compositions and administered to a mammalian host, such as a human patient in a variety of forms adapted to the chosen route of administration, i.e., orally or parenterally, by intravenous, intramuscular, topical or subcutaneous routes. It is to be understood that the term pharmaceutically acceptable carrier also includes carriers that are suitable for topical use as described herein below. In one embodiment of the invention the pharmaceutically acceptable carrier is a dermatologically acceptable carrier.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds of formula I or formula II can be formulated as dermatological compositions and applied to a mammalian host, such as a human by a topical route. For topical administration, the present compounds may be applied in pure form, i.e., when they are liquids. However, it will generally be desirable to administer them to the skin as compositions or formulations, in combination with a dermatologically acceptable carrier, which may be a solid carrier or a liquid carrier.

Useful solid carriers include finely divided solids such as talc, clay, microcrystalline cellulose, silica, alumina, cyclodextrins and the like. Useful liquid carriers include water, alcohols or glycols or water-alcohol/glycol blends, in which the present compounds can be dissolved or dispersed at effective levels, optionally with the aid of non-toxic surfactants. Additional carriers include vegetable oils, hydrocarbon oils and waxes, silicone oils, animal and marine fats or oils. Adjuvants such as fragrances and additional antimicrobial agents can be added to the composition to optimize the properties for a given use. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Cosmetic compositions, may contain conventional ingredients known to those of ordinary skill in the art, such as those described in Kirk-Othmer, Encyclopedia of Chemical Technology, Third Edition (1979), Vol. 7, pages 143-176. Specific ingredients, including typical sunscreens, are listed in, for example, the above mentioned Kirk-Othmer Encyclopedia, at pages 153-154. In addition, topical preparations and cosmetic formulations may be prepared as described in U.S. Pat. Nos. 4,199,576, 4,136,165, and 4,248,861. Examples of additional useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The percentage of the compositions and preparations may be varied. In general, a suitable dermatological composition will typically comprise a compound of formula I or formula II or a mixture thereof and may conveniently be between about 2-12% of the weight of a dermatological composition. The amount of active compound in such dermatological useful compositions is such that an effective level of compound will be obtained and/or maintained for the desired duration of action.

Skin is the body's largest organ and is constantly under attack due to endogenous and exogenous factors. Amongst all the exogenous factors that cause photo-damage to the skin, ultraviolet radiation plays an important role in damaging the integrity of the skin as demonstrated by various studies (*Photochemisty and Photobiology* 2002, 76, 561-69).

Sunscreens protect the DNA by reducing the absorption of sun's ultraviolet radiation to the epidermis. In the event of DNA damage, the repair mechanisms become essential for prevention against replication errors. DNA repair enzymes play a major role in reducing the DNA malignancies.

The activity of the enzymes involved in the DNA damage repair is crucial for over all genome integrity. The enzyme xpc is an important enzyme involved in the recognition and repair of DNA photoproducts in the nucleotide excision repair (NER) pathway. This particular enzyme (xpc) is also known to repair the DNA damage caused by the oxidative stress and UVA radiation [*Mutation Research* (2011) 728 (3) 107-117; *The EMBO Journal* (2006) 25, 4305-4315]. Our skin agents not only protect the DNA by absorbing UV light but also have shown to stimulate the essential repair enzyme, xpc involved in the first step of the DNA damage-repair signaling cascade.

Upon absorption of UV from sun light, the chemical ingredients present in commercial sunscreens can be broken down to form photo-products which can react with DNA to form cross links that are potentially toxic [Butt, S. T & Christensen, T; *Toxicity and Phototoxicity of Chemical Sun Filters*: Radiat Prot Dosimetry (2000) 91 (1-3): 283-286]. There has been a continuous demand for safer and novel sunscreens that work by unique mechanisms of action like and with the option of added benefits such as anti-aging and DNA repair enzyme stimulation.

The compounds of formula I and formula II and dermatological compositions thereof as described above can be used in sunscreens or other cosmetic formulations specifically contemplated for the purpose of protecting skin or DNA in skin from photodamage or for repairing photodamaged skin or photodamaged DNA in the skin. It is apparent to those of ordinary skill in the art that the compositions or formulations can be in many forms, including, but not limited to, for example, solutions, lotions, oils, sprays, creams, pastes, emulsions, sprays, or aerosols and delivered in a suitable manner.

Photodegradation is one of the factors for skin aging apart from the physiological changes that occur in the skin. Skin aging slows down the production of some key components of extra-cellular matrix. The agents of the present invention can not only help protect the skin from UV damage but also initiate the cellular repair processes and therefore can also be used to stimulate the production of key factors such as collagen, elastin and hyaluronic acid involved in the skin aging processes.

In sunscreen or suntan lotion formulations it may be advantageous to include an effective amount of the compounds described in the present invention (e.g. one or more compounds of formula I or formula II) in combination with other conventional sunscreen agents. Other sunscreen agents include but are limited to avobenzone, ecamsule, methylanthranilate, oxybenzone, dioxybenzone, sulisobenzone, octinoxate, homosalate, octocrylene and octylsalate.

It has been determined that the compounds of formula I absorb UV light at the same wavelength that DNA absorbs UV light. Upon exposure of UV light a compound of formula Ia, Ic, or Ie is converted to a corresponding compound of formula Ib, Id or If respectively. Accordingly, the compounds of formula Ia, Ic or Ie may be useful to protect DNA in the skin of a mammal (e.g. a human) from damage such as UV damage (e.g. UV-B) damage. In another embodiment of the invention the compounds of formula Ia, Ic or Ie can protect skin from photodamage. It has also been discovered that compounds of formula Ia, Ic or Ie can stimulate DNA repair enzymes. Accordingly, in another embodiment the compounds of formula Ia, Ic or Ie may be useful for the repair of photodamaged skin or for the repair of photodamaged DNA.

The exposure level of ionizing radiation has grown significantly with the use of tools like radiation therapy and X-rays. In addition, exposure can also occur at nuclear reactor sites. Exposure to radiation can produce a variety of lesions in DNA including crosslinks and formation of dimers. Accordingly, effective anti-radiation drugs are urgently needed (e.g. drugs that can prevent or treat ionizing radiation damage). Repair of damage to DNA is of central importance to all cells and stimulation of these repair mechanisms may be useful antiradiation therapy. Certain compounds of the instant invention (e.g. compounds of formula Ia, Ic or Ie) are known to increase the cellular production of DNA repairing enzymes. Accordingly, these compounds may have therapeutic utility for preventing or treating ionizing radiation damage in mammals.

The ability of a compound of the invention to protect DNA from photodamage may be determined using pharmacological models which are well known to the art, or using Test A or Test B described below.

Test A. DNA Protection Assay (Solution)

Black tandem cuvettes were used in the following experiments. Black tandem cuvettes (NSG Precision Cells Farmingdale, N.Y.; Cat#56UV10) are standard 1 cm×3 cm cuvettes which have been divided into 2 chambers. Each chamber holds approximately 1.5 mL of liquid. All windows and the partitions were polished and 3 sides were wrapped with black electrical tape leaving only one side for the UV light to go through and directing the light through the protective solutions (OUTER CHAMBER) and then onto inner solution (INNER SOLUTION).

DNA (100 μg pEGFP-C1 Plasmid DNA—Clontech/Takara) was placed in the INNER CHAMBER and protected by using 10 mM of compound 3a/24a or degassed water in the OUTER CHAMBER. The tandem cuvettes were then exposed to 1-300 nm UV bulbs in the Rayonet at 4° C. Aliquots (25 μL) of the DNA solution were taken at each time point (5, 10 or 15 minute intervals). The irradiated DNA was digested with T4 endonuclease V, an enzyme specific for thymidine dimer damage. The DNA was incubated for 1 hour at 37° C. in the presence of 20 U (1 μL) T4 Endonuclease V and then run on a 1% Agarose gel (1×TBE, 0.5 hr at 50V). The gel was then stained with Ethidium bromide and visualized using a BioRad Gel Documentation System.

Test B. B. DNA Protection Assay (Cream)

A small amount of the cream (0.1 cc) was applied to the outside of black tandem cuvettes and a quartz slide, cut to the size of the cuvette, was placed over the cream to make an even layer. The quartz cuvettes were wrapped in black electrical tape, leaving only one side for the UV light to go through and directing the UV light through the protective cream. The DNA was irradiated using cream vehicle alone or compound 3a/24a (5%) in cream vehicle.

DNA (100 μg pEGFP-C1 Plasmid DNA—Clontech/Takara) was placed in the OUTER CHAMBER and protected by the cream applied to the outside of the cuvette. The tandem cuvettes were exposed to 1-300 nm UV bulbs in the Rayonette at 4° C. Aliquots (25 μL) of the DNA solution were taken at each time point (5, 10 or 15 minute intervals). The irritated DNA was digested with T4 endonuclease V, an enzyme specific for thymidine dimer damage. The DNA was incubated for 1 hour at 37° C. in the presence of 20 U (1 μL) T4 Endonuclease V and then run on a 1% Agarose gel (1×TBE, 0.5 hr at 50 V). The gel was stained with Ethidium bromide and visualized using a BioRad Gel Documentation System.

The ability of a compound of the invention to protect DNA in cells may be determined using pharmacological models which are well known to the art, or using Test C.

Test C. Cell Protection Assay (Cream)

RPMI-8226 cells (2.5×$10^6$ cells/mL) were placed in 3 mL quartz black cuvettes with a stir bar in the bottom of the cuvette to keep the cells in uniform suspension during the experiment. The quartz cuvettes are wrapped in black electrical tape, leaving only one side for UV light to go through. A small amount of the cream (0.1 cc) was applied to the outside of the black tandem cuvettes and a quartz slide, cut to the size of the cuvette, was placed over the cream to make an even layer and UV light was directed through the protective cream. The cells were exposed to 1-300 nm UV bulb at 4° C. in the Rayonette with continuous stirring by a stir plate. At each timepoint, (15 and 30 minute intervals) a cuvette containing cells was removed from the Rayonette. The cells were protected by using cream vehicle or compound 3a/24a (5%) in cream vehicle.

Post exposure, the cells were transferred to sterile 1.7 mL tubes and the cuvettes were washed with 1×500 µL PBS and the contents were transferred to the corresponding sterile 1.7 mL tube. The tubes were centrifuged for 2 minutes at 13K rpm and 4° C., the supernatant was decanted and the cell pellets resuspended in Proteinase K. The tubes were incubated for 3 hrs at 55° C. (to overnight) and the DNA was isolated using the Isolation of DNA from Whole Cells Protocol. The isolated DNA was digested with T4 endonuclease V, (1 hr, 37° C.) and run on a 1% Agarose gel (1×TBE, 1 hr at 50 V). The gel was stained with Ethidium bromide and visualized using a BioRad Gel Documentation System.

The compounds that were examined in for tests A, B and C including compounds of the invention are shown in Table I.

TABLE I

| | in vitro assays | | |
|---|---|---|---|
| | plasmid DNA | | |
| Compound # | AR in water Test A | AR in cream Test B | Cells AR in cream Test C |
| 3a | X | X | X |
| 3b | X | | |
| 3c | X | | |
| 3d | X | | |
| 8 | X | X | |
| 10 | | | |
| 9a, 9b & 9c | X | | |
| 24a, 24b, 24c, 24d, 24e & 24f | X | X | |
| 28 | X | | |
| 32 | X | | |

(Compounds that were examined in a test are denoted by an "x")

The compounds that were tested in tests A, B and C protected DNA from UV-induced damage for longer periods of time when compared to controls. These results demonstrate that compounds of the invention protect DNA from photodamage. Accordingly compounds of the invention may be useful as dermatological agents for the prevention of DNA damage in a variety of forms including sunscreens and cosmetics.

The ability of a compound of the invention to protect animal skin may be determined using pharmacological models which are well known to the art, or using Test D.

Test D. Murine Animal Studies

In accordance with IACUC Code Number: 0902A60149, 6-8 weeks old SKH-1 were housed in RAR housing and did not receive any sunlight prior to the study. The UVA, UVB and Solar Simulated Light (SSL) treatment groups included mice that were left untouched in their cages (no preventative treatment) and mice treated topically on their backs with cream vehicle or AR compounds in the cream vehicle and rubbed with a glove. At 20 minutes post treatment the mice were exposed to 180 mJ/cm$^2$ of UVA, UVB or SSL equivalent to one hour of noon day summer sunlight. One, four, eight and twenty-four hours post UVA, UVB or SSL exposure, the mice were euthanized by IP Ketamine/Xylazine injection and bled. The serum was collected and sent to the Diagnostic Center for Population and Animal Health (DCPAH) at Michigan State University for 25-Hydroxyvitamin D analysis and the Diagnostic Labs at the University of Minnesota—Veterinary Medical Center for Small Animal Profile Panel.

The no UVA, UVB and SSL treatment groups included mice which were left untouched in their cages (no preventative treatment) and mice treated topically on their backs with cream vehicle and AR compounds in cream vehicle as indicated above. After treatment the mice were placed back into their cages, away from sunlight. One, four, eight and twenty-four hours post treatment, the no UVA, UVB and SSL treated mice were euthanized by IP Ketamine/Xylazine injection and bled. The serum was collected and sent to the Diagnostic Center for Population and Animal Health (DCPAH) at Michigan State University for 25-Hydroxyvitamin D analysis and the Diagnostic Labs at the University of Minnesota—Veterinary Medical Center for Small Animal Liver and Kidney Function Profile.

For the animal groups above, post euthanasia, the dorsal and belly skin was collected and preserved in Zamboni's fixative for future studies. Skin samples are sent to the Masonic Cancer Center Comparative Pathology Shared Resource at the University of Minnesota for H&E staining to look for skin irritation. The skin was analyzed in-house by immunohistostaining (p53, thymine dimer, XPC and other DNA repair enzymes, collagen, elastin, etc.) and confocal microscopy.

Murine Animal Model Testing Results (UV Protection of SKH-1 Hairless Mouse Dorsal Skin by Compound 3a/24a):

Compound 3a (0.5%) in DMSO was topically applied to SKI-1-1 hairless dorsal skin and irradiated with UVB (6 Kj/m$^2$ (8.33 minutes). This dosage is above the minimal erythemal dose (MED) of ~3.5 kJ/m2 and is equivalent to single sunburn. There were two control groups of mouse present in this study, untreated—no vehicle, no drug, no UV and UV exposure only group. These mice were treated with a topical application of our compound 3a and showed a significant protection against UV as compared to the UV only control which had shown the thymine dimer formation (DNA damage). The second control group (untreated—no vehicle, no drug, no UV) remains unaffected.

Compound 3a (0.5%) in cream vehicle was topically applied topically to SKH-1 hairless mouse dorsal skin and exposed to UVB light. Approximately 100 µl (0.1 cc) of each formulation was applied to mouse dorsal skin 20 minutes prior to UVB exposure. The treatment groups received the standard dose of 6 Kj/m$^2$ and were harvested 4 hours after irradiation. At harvest, dorsal skins were removed and fixed in zamboni fixative. 5% of 3a in cream vehicle protected against thymine dimer formation as compared to the UV only control.

Compound 24a (5% w/w) in cream vehicle was topically applied topically to SKH-1 hairless mouse dorsal skin and exposed to UVB light. Approximately 100 µl (0.1 cc) of each formulation was applied to mouse dorsal skin 20 minutes prior to UVB exposure. The treatment groups received the standard dose of 6 KJ/m$^2$ and were harvested 4 hours after irradiation. At harvest, dorsal skins were removed and fixed in zamboni fixative. In this experiment, 5% of 24a in cream vehicle protected against thymine dimer formation (DNA damage) as compared to the UV only control.

Up-Regulation of Key DNA Repair Enzyme (xpc) by Compound 3a/24a with SSL (Solar Simulated Light):

Compound 3a (5%) in cream vehicle was applied topically to SKH-1 hairless mouse dorsal skin and exposed to 6 KJ/m$^2$ of solar simulated light (SSL) that is equivalent to 1 h noon time summer sun light. In this experiment 5% 3a in cream stimulated xpc production in SSL exposed SKH-1 hairless mouse dorsal mice skin. This suggests that the dimers formed by compound 3a upon exposure to SSL are recognized by DNA repair enzymes and stimulated more xpc repair enzyme in the presence of SSL as compared to SSL cream—only control. A compound that stimulates xpc production not only has sunscreen benefits, but could prove therapeutic in the treatment of xeroderma pigmentosum, a genetic disorder of DNA repair in which the ability to repair damage caused by UV light is detrimental.

Compound 24a (5%) in cream vehicle was applied topically to SKH-1 hairless mouse dorsal skin and exposed to 180 mJ/cm$^2$ of solar simulated light (SSL) that is equivalent to 1 h noon time summer sun light. In this experiment, 5% of 24a in cream stimulated xpc production in SSL exposed SKH-1 hairless mouse dorsal mice skin. This suggests that the dimers formed by compound 24a upon exposure to SSL are recognized by DNA repair enzymes and stimulated more xpc repair enzyme in the presence of SSL as compared to SSL cream—only controls. A compound that stimulates xpc production not only has sunscreen benefits, but could prove therapeutic in the treatment of xeroderma pigmentosum, a genetic disorder of DNA repair in which the ability to repair damage caused by UV light is detrimental.

Up-Regulation of Key DNA Repair Enzyme (Xpc) by Compound 10 without Exposing Skin to SSL (Solar Simulated Light):

Compound 10 (5%) in the cream vehicle was topically applied to SKH-1 hairless mouse dorsal skin and did not receive SSL irradiation. The mice were placed back in their cages, away from sunlight and euthanized—1 hour 20 minutes, 4 hours 20 minutes, and 8 hours 20 minutes post application. The purpose of this experiment was to see if compound 10 can stimulate DNA repair enzymes. The 8 hour time point skin section was completely negative for thymine dimer immuno-reactivity. This is important as it shows that the dimer antibody is not recognizing dimers formed by compound 3a, it is only reactive with innate dimers. The DNA repair enzyme, xpc which is stimulated in response to UV-induced DNA damage and the initiator of a cascade of other repair enzymes, showed significant immuno-reactivity with xpc antibody. This suggests that the dimers formed by compound 3a exposure to SSL are recognized by the immune system and are able to stimulate xpc repair enzyme in the absence of UV damage. Mice treated with compound 3a in cream exposed to SSL have xpc levels above baseline levels for SSL only treated controls in mice.

The ability of a compound of the invention to protect human skin may be determined using pharmacological models which are well known to the art, or using Test E.

Test E. Human Skin Study

Human skin was obtained from the University of Minnesota BioNet Tissue Procurement Facility and stored on ice or in cell culture media until ready to be used. All samples were kept away from sunlight. The skin was cut into pieces and placed in 6-well cell culture plates with a small amount of culture media at the bottom of the well but not enough to cover the top of the tissue. Using a gloved hand, the skin was rubbed with cream vehicle or AR drug in the cream vehicle. At 20 minutes post treatment the skin was exposed to 180 mJ/cm$^2$ of UVA, UVB or Solar Simulated Light (SSL) equivalent to one hour of noon day summer sunlight. Post UVA, UVB or SSL exposure, additional media was placed in the bottom of the wells and the plates moved to the tissue culture incubator (37° C., 5% $CO_2$). Samples were removed from the incubator and placed in Zamboni's fixative for future studies at one, four, eight and twenty-four hours post UVA, UVB or SSL exposure.

Samples not exposed to UVA, UVB or SSL light were placed into 6-well plates with a small amount of cell culture media but not enough to cover the top of the tissue and stored in the cell culture incubator. The skin samples not exposed to UVA, UVB or SSL light were treated with cream vehicle and AR in cream vehicle as indicated above. At 20 minutes post treatment, the skin (in the plates) was moved into the cell culture incubator (37° C., 5% $CO_2$). Samples were removed from the incubator and placed in Zamboni's fixative for future studies at one, four, eight and twenty-four hours post treatment.

All skin samples were analyzed in-house by immunohistostaining (p53, thymine dimer, XPC and other DNA repair enzymes, collagen, elastin, etc.) and confocal microscopy.

Human Skin Model Testing Results:

Topical treatments of 5% 3a were applied to skin 20 minutes prior to SSL exposure. Control tissues did not receive any topical treatment or SSL and were kept in the incubator throughout the experiment. After compound incubation, tissues requiring SSL were placed under the SSL light box in growth media for 2 hours, or 180 mJ/cm2. After SSL exposure, tissue was placed back in incubator and incubated for 4 hours, then drop fixed in Zamboni's fixative. The tissue was cut and stained accordingly and the primary antibodies used were mouse monoclonal to thymine dimers. 5% of 3a in cream vehicle protected against thymine dimer formation as compared to the UV only control.

Compound 3a (5%) stimulated xpc production in UV exposed human skin. The experiment suggested that the dimers formed by compound 3a upon exposure to SSL were recognized by DNA repair enzymes and will stimulate more xpc repair enzyme in the presence of UV as compared to UV cream—only control. A compound that stimulates xpc production not only has sunscreen benefits, but could prove therapeutic for conditions such as xeroderma pigmentosum and individuals who are immunosuppressant (transplant & HIV patients).

The human skin treated with the dimerized compound 10 showed higher levels of xpc than the SSL only control. The non-dimerized 1,3TTP sample did not show any significant xpc staining in non-irradiated human skin tissue. Overall, the dimerized compound 10 stimulates xpc production in non SSL damaged human skin and this stimulation is still evident 8 hours post application. A compound that stimulates xpc production not only has sunscreen benefits but could also be a therapeutic in the treatment of xeroderma pigmentosum. The stimulation of the enzyme, xpc is also beneficial in the repair of DNA oxidative damage (BER) due to UVA radiation [*The EMBO Journal* 2006, 25, 4305-15].

Based on in vitro (plasmid DNA and cells) and in vivo (murine and human skin) data analysis the compounds not only protect against the harmful effects of UV radiation but also stimulate the key repair enzymes involved in DNA repair processes. The confocal and conventional epifluorescent images have been used to assess the thymine-thymine dimers (DNA damage) and the repair enzyme, xpc immunoreactivity in epidermal keratinocytes of dorsal skin sections from irradiated as well as non-irradiated mice and human skin.

The invention will now be illustrated by the following non-limiting Examples.

EXAMPLES

All chemicals were purchased from Sigma Chemicals, St. Louis, Mo. All compounds were characterized by 1H NMR, 13C NMR, mass and melting point analysis. Nuclear Magnetic Resonance spectra were recorded on a Varian XL 600 MHz instrument. All 1H and $^{13}$C NMR experiments are reported in units, parts per million (ppm), and were measured relative to residual DMSO in the deuterated solvent. All coupling constants were reported in Hz. Melting points were determined on Mel-Temp II apparatus and are uncorrected. Mass analyses were performed on Agilent LC-TOF 1100 mass spectrometer equipped with either an ESI or APCI source.

Example 1

Preparation of Compounds 3a, 3b, 3c and 3d

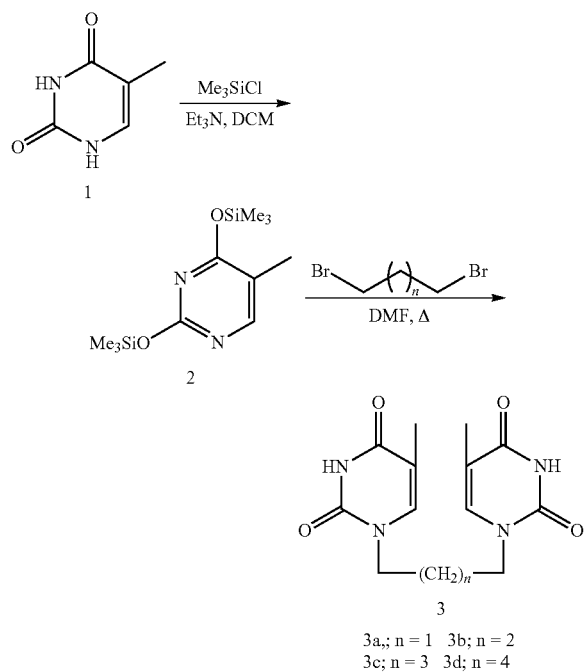

To a solution of 1,3-dibromopropane (2.202 g, 10.07 mmol) in 50 mL of anhydrous DMF was added O,O'-Bis (trimethylsilyl)-thymine (2) (6.256 g, 23.17 mmol). The solution was heated to 170° C. and stirred overnight. The reaction was cooled to 0° C. and 10 mL of water was added to the reaction mass to precipitate the product. The precipitated mass was stirred for 15 min at 0° C. The solids were filtered off, washed with 100 mL of chloroform-methanol (1:1) and dried under vacuum to give compound 3a (2.351 g, 81%) as an off white solid. $^1$H NMR (600 MHz, DMSO-d$^6$): δ 11.20 (s, 2H), 7.51 (s, 2H), 3.71 (t, 4H, J=7.04 Hz), 1.91 (t, 4H, J=7.04 Hz), 1.73 (s, 6H); $^{13}$C NMR (150 MHz, DMSO-d$^6$): δ 164.72, 151.36, 141.68, 108.98, 45.27, 28.31, 12.37; Mass (ESI-MS): 293.154 (M+H); m.p: 330-334° C.; Compounds 3b, 3c and were prepared following the procedure described for compound 3a. 3b: $^1$H NMR (600 MHz, DMSO-d$^6$): δ 11.18 (s, 2H), 7.50 (s, 2H), 3.62 (br, 4H), 1.73 (s, 6H), 1.53 (br, 4H); $^{13}$C NMR (150 MHz, DMSO-d$^6$): δ 164.71, 151.35, 141.86, 108.90, 47.16, 25.84, 12.37; Mass (ESI-MS): 307.157 (M+H); m.p: 348-350° C.; 3c: $^1$H NMR (600 MHz, DMSO-d$^6$):): δ 11.15 (s, 2H), 7.47 (s, 2H), 3.57 (t, 4H, J=7.05 Hz), 1.71 (s, 6H), 1.55 (quintet, 4H, J=7.05 Hz), 1.19 (br quintet, 2H, J=7.05 Hz); $^{13}$C NMR (150 MHz, DMSO-d$^6$): δ 164.70, 151.29, 141.85, 108.82, 47.37, 28.48, 23.12; 12.36; Mass (ESI-MS): 321.174 (M+H); m.p: 250-252° C.; 3d: NMR (600 MHz, DMSO-d$^6$): δ 11.14 (s, 2H), 7.48 (s, 2H), 3.56 (t, 4H, J=7.04 Hz), 1.71 (s, 6H), 1.52 (br quintet, 4H, J=7.05 Hz), 1.22 (br quintet, 4H, J=7.04 Hz); $^{13}$C NMR (150 MHz, DMSO-d$^6$): δ 164.71, 151.29, 141.82, 108.82, 47.42, 28.77, 25.87; 12.35; Mass (ESI-MS): 354.141 (M+H); m.p: 233-235° C.

Example 2

Preparation of Compound 8

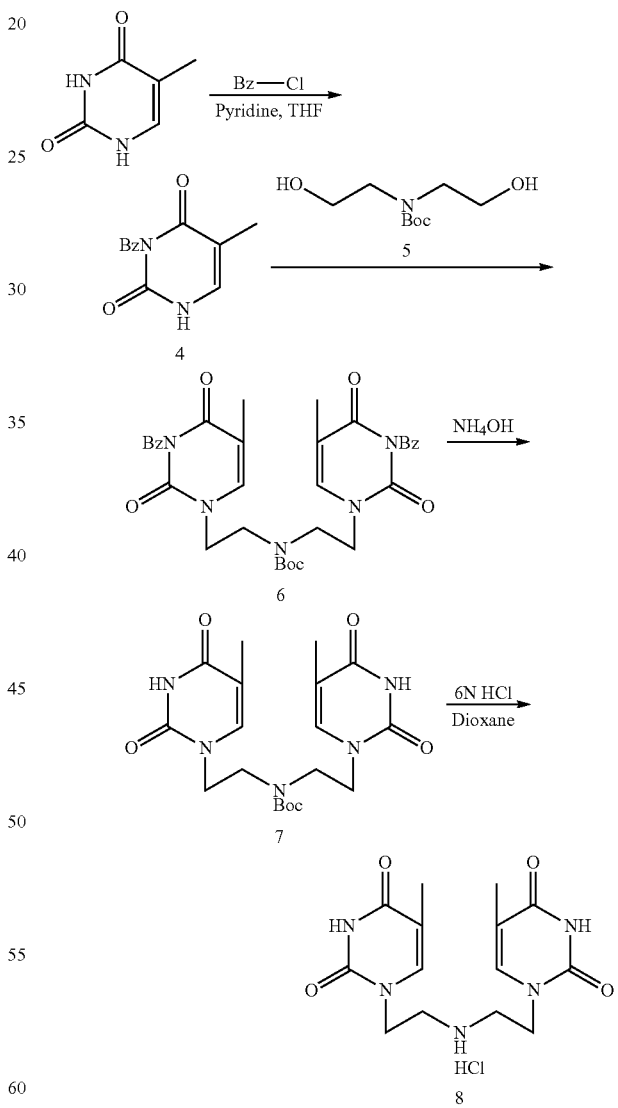

To a solution of thymine (1) in THF was added pyridine and the reaction was cooled to 0° C. Benzoyl chloride was added carefully at 0° C. and the reaction was stirred overnight at room temperature. The reaction mass was evaporated to give the crude solid which was purified by SiO$_2$ flash chromatography to give the N3-benzoyl thymine (4) as a white solid. NMR (600 MHz, CD$_3$OD): δ 7.94 (m, 2H), 7.71 (t, 1H, J=7.3 Hz), 7.57 (m, 2H), 7.38 (s, 1H), 1.90 (s, 3H); Mass (ESI-MS): 231.22 (M+H); m.p: 178-180° C.

To a solution of N$^3$-benzoyl thymine in THF was added PPh$_3$ and DIAD and the reaction was cooled to at 0° C. Compound 5 in THF was added to the reaction mass dropwise and the reaction was slowly brought to room temperature. Stirring was continued overnight. The organic solvents were evaporated to give the dark brown residue which was purified by SiO$_2$ flash chromatography to give the NBz-bisthymine compound 6. $^1$H NMR (600 MHz, DMSO-d$^6$): δ 7.91 (m, 4H), 7.74 (t, 2H, J=7.3 Hz), 7.67 (s, 2H), 7.56 (m, 4H), 3.74 (t, 4H, J=Hz), 2.79 (t, 4H, J Hz), 1.79 (s, 6H), 1.43 (s, 9H); $^{13}$C NMR (150 MHz, DMSO-d$^6$): δ 170.36, 163.49, 163.25, 155.57, 150.01, 149.86, 143.07, 135.82, 135.78, 131.85, 131.57, 130.96, 130.60, 129.89, 129.64, 108.78, 108.11, 79.92, 47.12, 45.67, 44.34, 43.12, 28.15, 12.37, 12.22; Mass (ESI-MS): 630.33 (M+H); m.p: 164-166° C.

Compound 6 was dissolved in aqueous ammonia and stirred overnight at room temperature. The reaction was evaporated under vacuum to give the off-white solid which was purified by SiO$_2$ flash chromatography to give the intermediate 7. $^1$H NMR (600 MHz, DMSO-d$^6$): δ 7.93 (s, 1H), 5.56 (t, 1H), 5.21 (s, 1H), 5.06 (m, 1H), 4.99 (m, 1H), 4.36 (m, 1H), 4.06 (m, 1H), 3.84 (m, 2H), 3.58-3.51 (m, 2H), 2.86 (s, 3H), 2.71 (s, 3H), 1.51 (s, 9H); $^{13}$C NMR (150 MHz, DMSO-d$^6$): δ 162.75, 157.15, 154.08, 151.74, 135.97, 117.46, 117.14, 86.76, 85.62, 74.13, 70.08, 61.83, 36.22, 31.23, 25.56; Mass (ESI-MS): 422.43 (M+H); m.p: 254-256° C.

Compound 7 was dissolved in a solution of 6N HCl in dioxane and water (1:1) and stirred at 25° C. overnight. The solvents were evaporated under vacuum to give an oily residue which was obtained as white solid 8 after repeated evaporations with toluene. $^1$H NMR (600 MHz, DMSO-d$^6$): δ 11.23 (s, 2H); 8.01 (s, 1H), 5.74 (t, 1H), 5.47 (s, 1H), 5.68 (m, 1H), 5.01 (m, 1H), 4.93 (m, 1H), 4.53 (m, 1H), 4.01 (m, 2H), 3.85-3.65 (m, 2H), 2.95 (s, 3H), 2.85 (s, 3H); $^{13}$C NMR (150 MHz, DMSO-d$^6$): δ 165.81, 159.17, 155.80, 152.65, 136.01, 118.23, 117.94, 88.23, 86.75, 74.93, 71.48, 62.05, 36.76, 31.94; Mass (ESI-MS): 322.23 (M+H); m.p: >320° C.

Example 3

Preparation of Compound 9

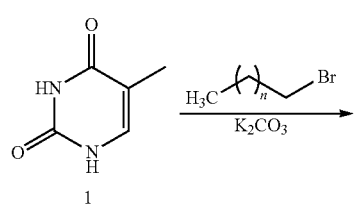

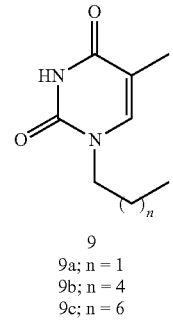

9
9a; n = 1
9b; n = 4
9c; n = 6

To a solution of thymine 1 (5.01 g, 39.76 mmol) in anhydrous DMSO (135 mL) was added 1-bromopropane (1.601 g, 13.01 mmol) and anhydrous potassium carbonate (5.50 g, 39.28 mmol) and the resulting suspension was stirred for 10-12 h at room temperature. The solids were filtered off and the filtrate was evaporated under reduced pressure at 50° C. leaving a colorless semisolid which was suspended 500 mL water and extracted with chloroform (3×125 mL). The organic layer was dried over anhydrous Na$_2$SO$_4$, filtered and evaporated to give the light yellow solid which was recrystallized using absolute ethanol to give white crystalline solid 9a (0.875 g, 40.13% based on 1-bromopraopane). $^1$H NMR (600 MHz, DMSO-d$^6$): δ 11.19 (s, 1H), 7.5 (s, 1H), 3.59 (t, 2H, J=7.04 Hz), 1.72 (s, 3H), 1.59 (app. sext, 2H), 0.82 (t, 3H, J=7.63 Hz); $^{13}$C NMR (150 MHz, DMSO-d$^6$): δ 164.72, 151.32, 141.93, 108.72, 49.09, 22.16, 12.34, 11.09; Mass (ESI-MS): 169.191 (M+H); m.p: 133-135° C.

Compounds 9b and 9c were prepared in following the procedure described for compound 9a. 9b: $^1$H NMR (600 MHz, DMSO-d$^6$): δ 11.16 (s, 1H), 7.49 (s, 1H), 3.56 (t, 2H, J=7.05 Hz), 5.56 (t, 1H), 1.71 (s, 3H), 1.50-1.51 (m, 2H), 1.20-1.24 (m, 6H), 0.82 (t, 21-1, J=7.04 Hz); $^{13}$C NMR (150 MHz, DMSO-d$^6$): δ 164.70, 151.28, 141.86, 108.78, 47.54, 31.26, 28.83, 25.89, 22.39, 14.27, 12.32; Mass (ESI-MS): 211.135 (M+H); m.p: 126-128° C.; 9c: $^1$H NMR (600 MHz, DMSO-d$^6$): δ 11.14 (s, 1H), 7.49 (s, 1H), 3.57 (t, 2H, J=7.63 Hz), 5.56 (t, 1H), 1.73 (s, 3H), 1.51-1.53 (m, 2H), 1.22 (m, 6H), 0.83 (t, 2H, J=7.04 Hz); $^{13}$C NMR (150 MHz, DMSO-d$^6$): δ 164.70, 151.29, 141.86, 108.78, 47.54, 31.62, 29.01, 28.86, 26.23, 22.49, 14.35, 12.33, Mass (ESI-MS): 354.141 (M+H); 239.210; m.p: 112-114° C.

Example 4

Preparation of Compound 10

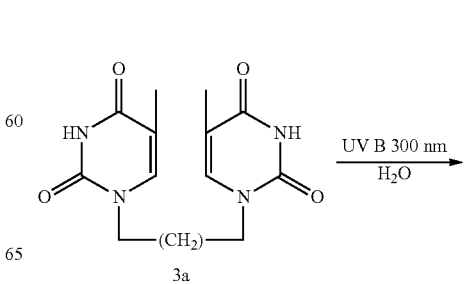

3a

-continued

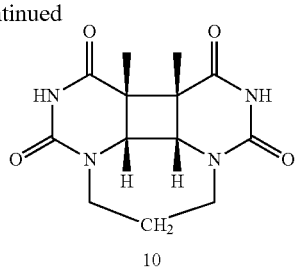

10

A solution of 3a (0.087 g, mmol) was dissolved in deionized water (175 mL, degassed) at 90° C., allowed to cool to room temperature in a 500 mL Pyrex flask. A stream of nitrogen was bubbled throughout the cooling to room temperature. The solution was irradiated at 300 nm in a Rayonett RPR 208 reactor and the reaction was monitored for the absorption at 270 nm with a 50:1 aliquot test solution every 1 h until reaction was complete (6 h). The irradiation was stopped and the round bottom flask was ca. taken out of the reactor. The pH was adjusted to 9 with aq.NaHCO$_3$. KMnO$_4$ (15 mg, 1.3 eq) was added and stirred at room temperature for 4-5 h. Saturated aq. NaSH (10 mL) precipitated MnO$_2$ which was removed by filtration. The carbonates in the filtrates were decomposed by careful addition of formic acid. Concentration of the solution to 30 mL furnished the photodimer as a crude product which was recrystallized from water to give the white solid 10 (0.048 g, 55.17%). $^1$H NMR (600 MHz, DMSO-d$^6$): δ 10.25 (s, 2H), 4.05 (d, 2H, J=12.91 Hz), 3.89 (m, 2H), 2.71 (m, 2H), 1.47-1.85 (m, 2H), 1.35 (s, 3H); $^{13}$C NMR (150 MHz, DMSO-d$^6$): δ 170.11, 151.29, 60.18, 46.99, 45.11, 23.96, 20.42; Mass (ESI-MS): 292.115 (M+H); m.p: >340° C.

Example 5

Preparation of Compound 11

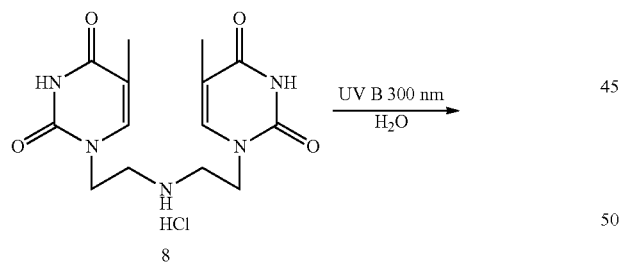

Compounds 11 were prepared in following the procedure described for compound 10 in Example 4. $^1$H NMR (600 MHz, DMSO-d$^6$): δ $^1$H NMR (600 MHz, DMSO-d$^6$): δ 10.23 (s, 2H), 5.45 (t, 1H), 5.47 (s, 1H), 5.68 (m, 1H), 5.01 (m, 1H), 4.93 (m, 1H), 4.53 (m, 1H), 4.01 (m, 2H), 3.85-3.65 (m, 2H), 2.95 (s, 3H), 2.85 (s, 3H); $^{13}$C NMR (150 MHz, DMSO-d$^6$): δ 165.81, 159.17, 155.80, 152.65, 136.01, 118.23, 117.94, 88.23, 86.75, 74.93, 71.48, 62.05, 36.76, 31.94; Mass (ESI-MS): 322.31 (M+H); m.p: >330° C.

Example 6

Preparation of Compound 12

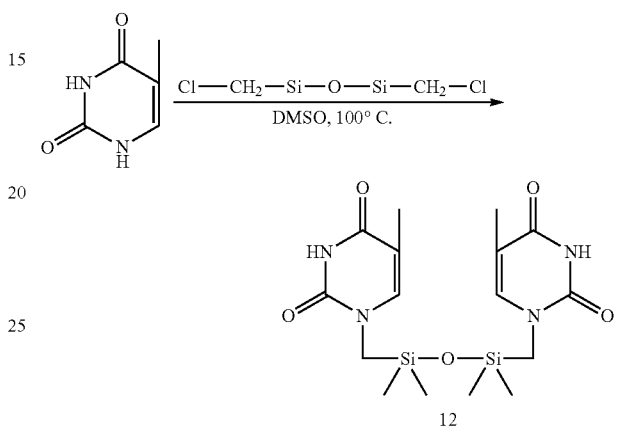

Sodium hydride (60% in mineral oil, 1.34 g, 54.33 mmol) was slowly added to a solution of thymine (6.025 g, 47.87 mmol) in dry DMSO (25 mL) and the mixture was stirred for 2 h at 50° C. Bis-chloromethyl-1,1,3,3-tetramethyldisiloxane (5.021 g, 21.73 mmol) was added and the mixture was heated for 3 days at 100° C. Reaction was brought to RT and 20 mL water was added. The reaction mass was extracted with ethyl acetate (3×50 mL) The organic layer was washed with water, brine and dried over anhydrous Na$_2$SO$_4$. The organic layer was filtered and dried under vacuum to yield the crude compound as white syrup which was recrystallized using a mixture of ethanol and ethyl acetate (9:1) and stored at −20° C. The precipitated compound was filtered and washed with 20 mL ethanol and dried under vacuum to give a white solid (6.35 g, 32.5%). $^1$H NMR (600 MHz, DMSO-d$^6$): δ (ppm) 11.14 (s, 1H), 10.89 (s, 1H), 7.30 (s, 1H), 3.09 (s, 4H), 1.64 (s, 7H), 0.00 (s, 12H); $^{13}$C NMR (150 MHz, DMSO-d$^6$): δ 164.93, 151.50, 137.73, 108.15, 45.14, 11.92, 0.00; Mass (APCI Neg.): 409.15 (M−H); m.p: 288-290° C.

Example 7

Preparation of Compound 13

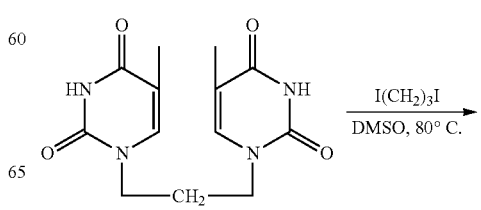

-continued

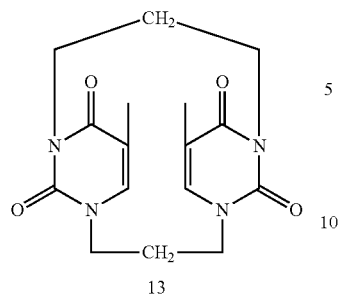

13

Sodium hydride 60% in oil (0.43 g, 10.7 mmol) was added to a suspension of 1,1' trimethylenebisthymine (1.51 g, 5.1 mmol) in dimethyl sulfoxide (80 mL) and stirred overnight at 60-65° C. 1, 3-Diiodopropane (1.63 g, 4.8 mmol) was added to the reaction mixture and stirred for 3 days at 80° C. to give a clear solution. The solvent was evaporated; the residual solid was washed with potassium carbonate aqueous solution (30 mL), methanol (20 mL), and diethyl ether (20 mL). The product in was purified by silica gel column using ethyl acetate/methanol as eluents to give the cyclic compound, II as a white solid (0.204 g, 12%). $^1$H NMR (600 MHz, CDCl$_3$, ppm): 7.05 (s, 2H, C6-H), 4.07 (t, 3H, N3-CH2), 3.75 (t, 4H, N1-CH2), 2.15 (t, 2H, N3-C—CH2), 1.98 (t, 2H, N1-C—CH2), 1.89 (s, 6H, C5-CH3); $^{13}$C NMR (150 MHz, CDCl$_3$): 164.11, 152.53, 141.21, 108.15, 51.20, 45.73, 28.20, 26.35, 10.35; Mass (APCI-Neg): 331.13 (M−H)

Example 8

Preparation of Compounds 24a, 24b, 24c, 24d, 24e, and 24f

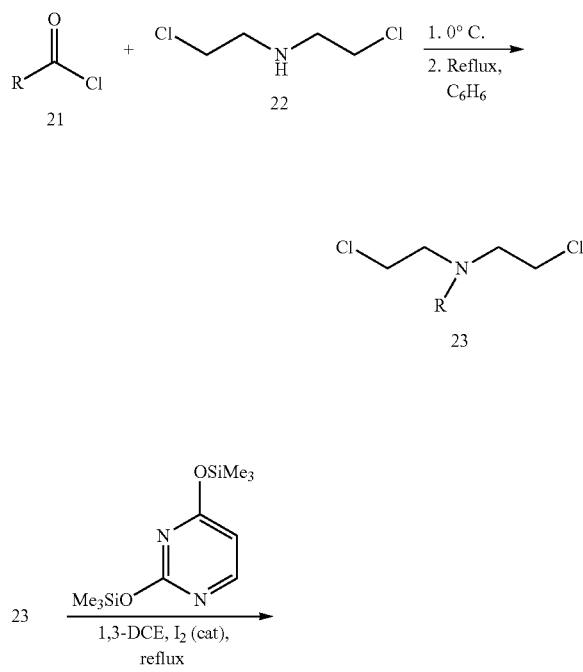

-continued

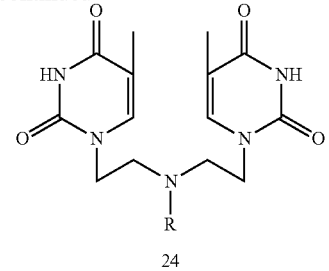

24
R = C$_3$H$_7$CO (24a);
C$_{15}$H$_{31}$CO (24b);
C$_{17}$H$_{35}$CO (24c)
Benzoyl (24d)
Cinnamoyl (24e)
OMe-cinnamoyl (24f)

To a solution of Bis-(chloroethyl)amine, 22 (1.393 g, 9.816 mmol) in benzene (20 mL) was added butyryl chloride (0.523 g, 4.908 mmol) dissolved in 10 mL benzene at 0° C. and stirred for 15 min. The reaction mass was refluxed for 1 h, cooled to RT and the precipitate was filtered off. The filtrates were evaporated to give the corresponding amide 23 (0.752 g, 72.3%) as a colorless oil. $^1$H NMR (600 MHz, DMSO-d$^6$): δ 3.75 (t, 4H), 3.51 (t, 4H), 2.71 (t, 2H), 1.45 (m, 2H), 0.76 (t, 3H); Mass (ESI-MS): 212.143 (M+H).

Compound 23 (0.251 g, 1.189 mmol) was dissolved in anhydrous 1,2-dichloroethane (30 mL) at RT. O,O'-Bis(trimethylsilyl)-thymine (0.738 g, 2.733 mmol) was added in one portion followed by the addition of catalytic I$_2$ (14 mG, 0.05 eqv) and refluxed for 24 h. The reaction mass was evaporated to give the crude solid which was purified by SiO$_2$ flash chromatography to give the compound 24a (0.301 g, 70.82%) as an off white solid. $^1$H NMR (600 MHz, DMSO-d$^6$): δ 11.30 (s, 1H); 11.10 (s, 1H); 7.49 (s, 1H); 7.31 (s, 1H); 3.76 (t, 4H), 3.47 (t, 4H), 2.09 (t, 2H), 1.72 (s, 3H); 1.68 (s, 3H); 1.36 (t, 2H), 0.75 (t, 3H); $^{13}$C NMR (150 MHz, DMSO-d$^6$): δ 173.71, 164.41, 163.55, 152.23, 151.35, 141.74, 141.13, 109.23, 108.95, 57.74, 57.63, 47.63, 47.55, 35.84, 19.37, 13.55, 12.33, 12.21; Mass (ESI-MS): 392.19 (M+H); m.p: 298-300° C. Compounds 24b, 24c, 24d, 24e and 24f were prepared following the procedure described for compound 24a. 24b: $^1$H NMR (600 MHz, DMSO-d$^6$): δ 11.52 (s, 1H); 11.31 (s, 1H); 7.55 (s, 1H); 7.41 (s, 1H); 3.72 (t, 4H), 3.43 (t, 4H), 2.11 (t, 2H), 1.75 (s, 3H); 1.65 (s, 3H); 1.53 (t, 2H), 1.33 (m, 2H); 1.29-1.25 (m, 22H); 0.95 (t, 3H); $^{13}$C NMR (150 MHz, DMSO-d$^6$): δ 173.15, 163.23, 163.10, 151.54, 151.43, 140.15, 139.85, 110.23, 110.20, 58.32, 58.30, 47.53, 47.50, 47.41, 35.33, 32.33, 30.68, 29.77, 29.75, 29.73, 29.72, 29.70, 29.68, 29.65, 28.98, 28.03, 23.15, 15.15, 12.85, 12.73; Mass (ESI-MS): 560.41 (M+H); m.p: 285-288° C. 24c: 1H NMR (600 MHz, DMSO-d$^6$): δ 11.68 (s, 1H); 11.53 (s, 1H); 7.58 (s, 1H); 7.49 (s, 1H); 3.78 (t, 4H), 3.51 (t, 4H), 2.35 (t, 2H), 1.85 (s, 3H); 1.78 (s, 3H); 1.63 (t, 2H), 1.46 (m, 2H); 1.35-1.21 (m, 28H); 0.98 (t, 3H); $^{13}$C NMR (150 MHz, DMSO-d$^6$): δ 173.31, 163.95, 163.23, 151.73, 151.81, 141.16, 140.95, 110.55, 110.34, 58.54, 58.50, 47.64, 47.61, 47.58, 35.43, 32.41, 30.72, 29.82, 29.75, 29.63, 29.71, 29.67, 29.65, 29.64, 29.61, 29.58, 28.88, 28.53, 23.45, 15.24, 12.21, 12.13; Mass (ESI-MS): 588.51 (M+H); m.p: 310-312° C. 24d: $^1$H NMR (600 MHz, DMSO-d$^6$): δ 11.57 (s, 1H), 11.48 (s, 1H), 8.33-7.68 (m, 5H), 7.54 (s, 1H); 7.45 (s, 1H); 3.81 (t, 4H), 3.76 (t, 4H), 1.71 (s, 3H), 1.68 (s, 3H); $^{13}$C NMR (150 MHz, DMSO-d$^6$): δ 170.71, 151.20, 150.11, 140.82, 139.95, 136.35, 129.36, 128.85, 128.73, 127.63, 109.83, 108.95, 58.54, 58.35, 48.42, 48.38, 28.77, 25.87; 12.35, 12.25; Mass (ESI-MS): 426.14 (M+H); m.p: 320-322° C. 24e: $^1$H NMR (600 MHz, DMSO-d$^6$): δ 11.63 (s, 1H), 11.53 (s, 1H), 8.43-7.87 (m, 5H), 7.64 (s, 1H), 7.59 (s, 1H), 7.37 (s, 1H), 7.28 (s, 1H) 3.73 (t, 4H), 3.64 (t, 4H), 1.81 (s, 3H), 1.76 (s, 3H); $^{13}$C NMR (150 MHz, DMSO-d$^6$): δ 171.65, 152.21, 151.31, 142.24, 141.84, 140.55, 137.31, 130.26, 129.15, 129.13, 128.33, 120.33, 110.33, 110.51, 58.76, 58.55, 49.32, 49.71, 28.34, 26.67; 12.51, 12.45; Mass (ESI-MS): 452.17 (M+H); m.p: 315-317° C. 24f: $^1$H NMR (600 MHz, DMSO-d$^6$): δ 11.45 (s, 1H), 11.37 (s, 1H), 7.78-6.35 (m, 5H), 7.24 (s, 1H), 7.01 (s, 1H), 6.77 (s, 1H), 3.41 (t, 4H), 3.26 (t, 4H), 1.81 (s, 3H), 1.78 (s, 3H); Mass (ESI-MS): 482.45 (M+H); m.p: 298-300° C.

Example 9

Preparation of Compound 28

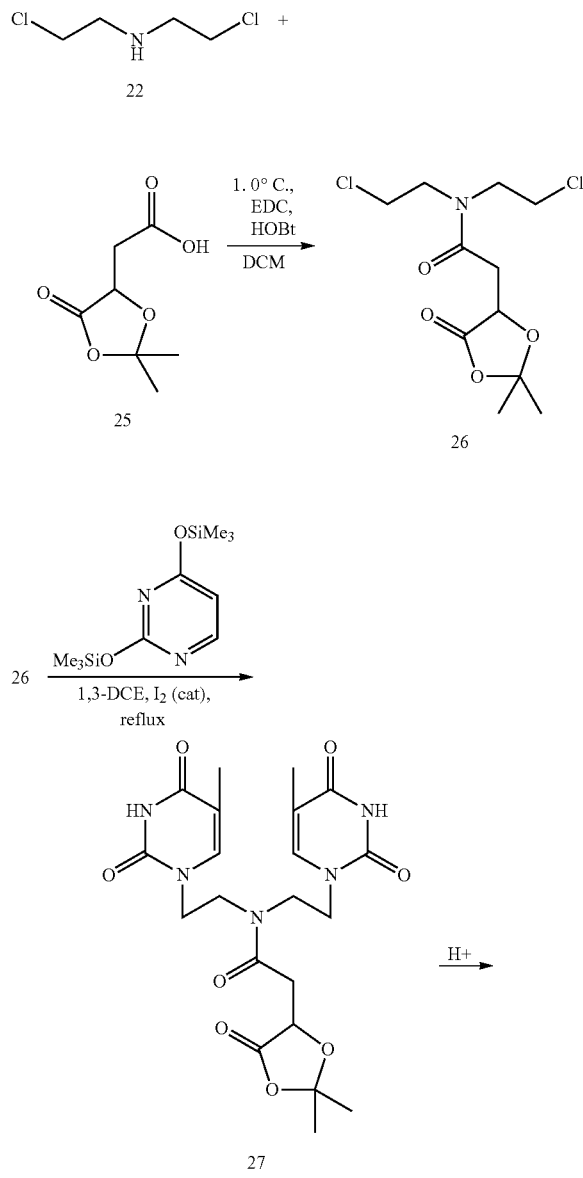

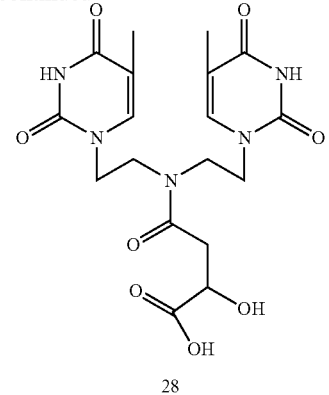

To a solution of acid 25 (1.752 g, 10.068 mmol) in anhydrous DCM (50 mL) was added 1-Ethyl-3-(3-dimethylaminopropyl) carbodiimide. HCl (2.922 g, 15.303 mmol) and N-hydroxybenzotriazole (2.038 g, 15.103 mmol) at 0° C. and stirred for 15 min. Bis-(chloroethyl) amine, 22 (1.511 g, 10.709 mmol) in DCM (10 mL) was added and the reaction mass was stirred overnight at RT. The reaction mass diluted with 50 mL of DCM and washed with aq. NaHO$_3$ solution (20 ml) and brine (20 mL). The organic layer was dried over anhydrous Na$_2$SO$_4$ and concentrated under vacuum to give the crude product which was purified by SiO$_2$ flash chromatography to give the compound 26 (2.651 g, 75%) as a colorless oil. $^1$H NMR (600 MHz, DMSO-d$^6$): δ 3.92 (t, 1H), 3.82-3.75 (m, 4H), 3.68 (m, 4H), 2.98-2.94 (dd, 2H), 1.55 (s, 3H), 1.59 (s, 3H); Mass (ESI-MS): 298.13 (M+H).

Compound 26 (1.253 g, 4.218 mmol) was dissolved in anhydrous 1,2-dcholoroethane (30 mL) at RT. O,O'-Bis(trimethylsilyl)-thymine (2.505 g, 9.281 mmol) was added in one portion followed by the addition of catalytic I$_2$ (20 mG, 0.05 eqv) and refluxed for 24 h. The reaction mass was evaporated to give the crude solid which was purified by SiO$_2$ flash chromatography to give the compound 27 (1.153 g, 56.79%) as an off white solid. $^1$H NMR (600 MHz, DMSO-d$^6$): δ 11.29 (s, 1H), 11.13 (s, 1H), 7.48 (s, 1H), 7.29 (s, 1H), 4.71 (t, 1H), 3.74-3.71 (m, 4H), 3.60-3.52 (m, 4H), 3.21-3.32 (m, 2H) 1.72 (s, 3H), 1.70 (s, 3H), 1.44 (s, 6H); Mass (ESI-MS): 478.67 (M+H); m.p: 285-287° C.

Compound 27 (0.851 g) was dissolved in 12N HCl in water and stirred overnight at RT. The reaction mass was concentrated under vacuum and the residue was freeze dried to obtain the compound 28 as white solid (0.725 g, 96%). $^1$H NMR (600 MHz, DMSO-d$^6$): δ 12.01 (br s, 1H), 11.36 (s, 1H), 11.23 (s, 1H), 7.57 (s, 1H), 7.37 (s, 1H), 4.34 (t, 1H), 3.82-3.75 (m, 4H), 3.71-3.58 (m, 4H), 3.31-3.28 (m, 2H), 2.83 (d, 1H), 1.79 (s, 3H), 1.80 (s, 3H), 1.78 (s, 6H); $^{13}$C NMR (150 MHz, DMSO-d$^6$): δ 176.15, 171.87, 153.14, 152.34, 142.65, 142.11, 140.96, 137.84, 131.25, 129.62, 129.33, 128.72, 120.84, 109.31, 109.85, 71.21, 58.54, 49.75, 36.23, 28.34, 26.54; 12.35, 12.29; Mass (ESI-MS): 438.77 (M+H); m.p: 321-323° C.

Example 10

Preparation of Compound 32

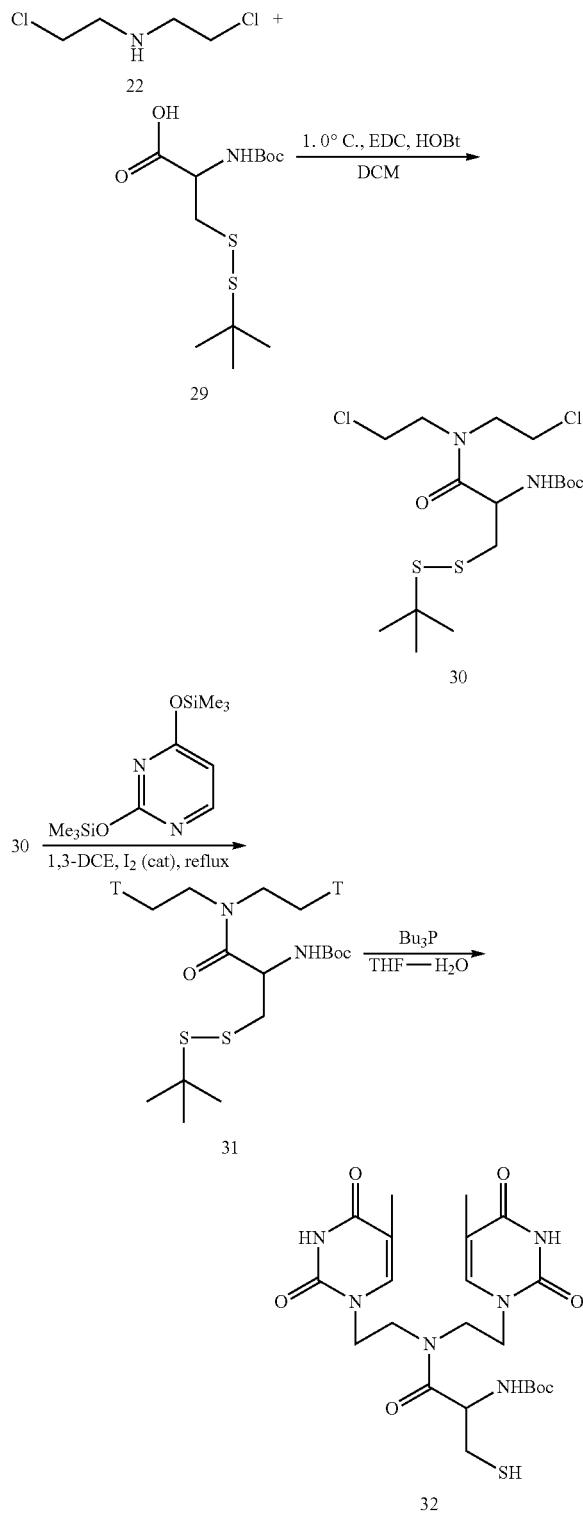

To a solution of acid 29 (1.250 g, 4.045 mmol) in anhydrous DCM (50 mL) was added 1-Ethyl-3-(3-dimethylaminopropyl) carbodiimide. HCl (0.819 g, 6.067 mmol) and N-hydroxybenzotriazole (1.158 g, 6.067 mmol) at 0° C. and stirred for 15 min. Bis-(chloroethyl)amine, 22 (0.684 g, 4.854 mmol) in DCM (10 mL) was added and the reaction mass was stirred overnight at RT. The reaction mass diluted with 50 mL of DCM and washed with aq. $NaHO_3$ solution (20 ml) and brine (20 mL). The organic layer was dried over anhydrous $Na_2SO_4$ and concentrated under vacuum to give the crude product which was purified by $SiO_2$ flash chromatography to give the compound 30 (1.035 g, 59.24%) as a colorless oil. $^1$H NMR (600 MHz, DMSO-$d^6$): δ 4.81 (m, 1H), 3.84-3.78 (m, 4H), 3.70-3.64 (m, 4H), 3.01-2.86 (dd, 2H), 1.43 (s, 9H), 1.34 (s, 9H); Mass (ESI-MS): 433.45 (M+H).

Compound 30 (0.752 g, 1.74 mmol) was dissolved in anhydrous 1,2-dichloroethane (50 mL) at RT. O,O'-Bis(trimethylsilyl)-thymine (1.445 g, 5.353 mmol) was added in one portion followed by the addition of catalytic $I_2$ (20 mG) and refluxed for 24 h. The reaction mass was evaporated to give the crude solid which was purified by $SiO_2$ flash chromatography to give the compound 11 (0.575 g, 55.82%) as an off white solid. $^1$H NMR (600 MHz, DMSO-$d^6$): δ 11.63 (s, 1H), 11.45 (s, 1H), 7.54 (s, 1H), 7.50 (s, 1H), 4.93 (m, 1H), 4.01-3.84 (m, 4H), 3.91-3.72 (m, 4H), 3.76-2.92 (dd, 2H), 1.75 (s, 6H), 1.51 (s, 9H), 1.45 (s, 9H); Mass (ESI-MS): 613.51 (M+H); m.p: 275-280° C.

Compound 31 (0.425 g, 0.857 mmol) was dissolved in THF-$H_2O$ (1:1) and tri-butyl phosphine (0.173 g, 1.027 mmol) was added and the reaction mass was stirred at RT for 24 h. The solvents were evaporated to give the crude solid which was purified by $SiO_2$ flash chromatography to give the compound 32 (0.245 g, 67.5%) as white solid. $^1$H NMR (600 MHz, DMSO-$d^6$): δ 11.74 (s, 1H), 11.65 (s, 1H), 7.36 (s, 1H), 7.31 (s, 1H), 5.01 (m, 1H), 4.17-4.01 (m, 4H), 3.98-3.81 (m, 4H), 3.76-3.52 (dd, 2H), 1.73 (s, 6H), 1.35 (s, 9H); $^{13}$C NMR (150 MHz, DMSO-$d^6$): δ 170.11, 163.65, 163.52, 155.81, 151.43, 151.38, 140.61, 110.32, 80.21, 58.67, 57.43, 47.81, 28.21, 28.18, 28.17 27.51, 12.25, 12.28; Mass (ESI-MS): 525.13 (M+H); m.p: 300-305° C.

Example 11

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
| --- | --- |
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
| --- | --- |
| Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
| --- | --- |
| Compound X = (free acid form) | 10.0 |
| Monobasic sodium phosphate | 0.3 |
| Dibasic sodium phosphate | 1.1 |
| Polyethylene glycol 400 | 200.0 |
| 1.0 N Sodium hydroxide solution (pH adjustment to 7.0-7.5) | q.s. |
| Water for injection | q.s. ad 1 mL |

| (vi) Aerosol | mg/can |
| --- | --- |
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

Example 12

The following illustrates a representative dermatological formulation containing a compound as described in Formula I or Formula II ('Compound X'), for therapeutic or prophylactic use in humans.

Cream: 2-12% Active ingredients (Compound X) and 88-98% Inactive ingredients

| Inactive Ingredients | % (w/w) |
| --- | --- |
| Water | 65 |
| Hexadecan-1-ol ($C_{16}H_{34}O$, Cetyl alcohol) | 3.0 |
| Octadecan-1-ol ($C_{18}H_{38}O$, Stearyl alcohol) | 8.5 |
| Isopropyl myristate ($C_{17}H_{34}O_2$) | 1.0 |
| Glycerine | 0.3 |
| Propylene glycol | 20.0 |
| Polysorbate 20 (TWEEN 20) | 2.0 |
| Isopropyl palmitate | 0.2 |
| Total for inactive ingredients | 100.00 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula I:

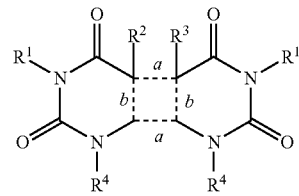

wherein:
each $R^1$ is independently H, $(C_1-C_6)$alkyl, $(C_3-C_7)$carbocycle or $R_aC(=O)—$, and the two $R^4$ groups together form a $—(C_3-C_8)$alkyl-group, a $—(C_2-C_6)$alkyl-Y—$(C_2-C_6)$alkyl-group or a $—(C_1-C_6)$alkyl-Y'—$(C_1-C_6)$alkyl-group; or each $R^4$ is independently H, $(C_1-C_6)$alkyl, $(C_3-C_7)$carbocycle or $R_aC(=O)—$, and the two $R^1$ groups together form a $—(C_3-C_8)$alkyl-group, a $—(C_2-C_6)$alkyl-Y—$(C_2-C_6)$alkyl-group or a $—(C_1-C_6)$alkyl-Y'—$(C_1-C_6)$alkyl-group; or the two $R^4$ groups together form a $—(C_3-C_8)$alkyl-group, a $—(C_2-C_6)$alkyl-Y—$(C_2-C_6)$alkyl group or a $—(C_1-C_6)$alkyl-Y'—$(C_1-C_6)$alkyl-group and the two $R^1$ groups together form a $—(C_3-C_8)$alkyl-group, a $—(C_2-C_6)$alkyl-Y—$(C_2-C_6)$alkyl-group or a $—(C_1-C_6)$alkyl-Y'—$(C_1-C_6)$alkyl-group;

the dashed bonds labeled "a" are absent and the dashed bonds labeled "b" are double bonds; or all the dashed bonds are single bonds;

$R^2$ is H, $(C_1-C_6)$alkyl or aryl, wherein aryl is optionally substituted with one or more $Z^1$ groups;

$R^3$ is H, $(C_1-C_6)$alkyl or aryl, wherein aryl is optionally substituted with one or more $Z^1$ groups;

Y is O, S, NH, $NR_c$, P, $P(=O)$ or POH;

Y' is $Si(R_b)_2$ or $—Si(R_b)_2—O—Si(R_b)_2—$;

each $R_a$ is independently $(C_1-C_6)$alkyl, $(C_3-C_7)$carbocycle or aryl, wherein aryl is optionally substituted with one or more $Z^1$ groups;

each $R_b$ is independently $(C_1-C_6)$alkyl, $(C_3-C_7)$carbocycle or aryl, wherein aryl is optionally substituted with one or more $Z^1$ groups;

each $R_c$ is independently $R_g$ or a $C_1-C_{18}$ saturated or unsaturated carbon chain that is optionally substituted with one or more groups independently selected from oxo (=O), hydroxy, mercapto, $(C_1-C_6)$alkoxy, $(C_1-C_6)$alkoxycarbonyl, $(C_1-C_6)$alkanoyloxy, $NR_dR_e$, carboxy, and aryl, wherein any aryl of $R_c$ is optionally substituted with one or more $R_f$;

each $R_d$ and $R_e$ is independently selected from H, $(C_1-C_6)$alkyl, $(C_1-C_6)$alkanoyl, phenyl, benzyl, and $R_g$;

each $R_f$ is independently selected from $(C_1-C_6)$alkyl, $(C_1-C_6)$alkoxy, $(C_1-C_6)$alkoxycarbonyl, $(C_1-C_6)$alkanoyloxy, $—C(=O)$-phenyl, and $—C(=O)CH_2C(=O)$-phenyl, wherein any phenyl is optionally substituted with one or more groups independently selected from $(C_1-C_6)$alkyl, $—SO_3H$, and $(C_1-C_6)$alkoxy;

each $R_g$ is

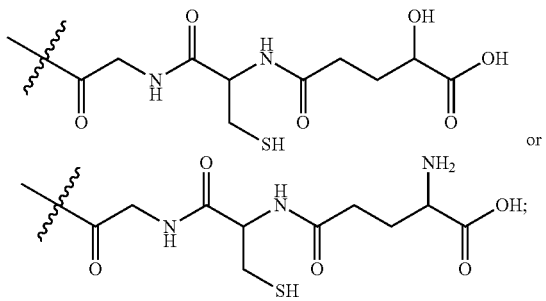

or each $Z^1$ is independently selected from $(C_1\text{-}C_6)$alkyl, halogen, —CN, —$OR_{n1}$, —$NR_{q1}R_{r1}$, —$NR_{n1}COR_{p1}$, —$NR_{n1}CO_2R_{p1}$, $NO_2$, —$C(O)R_{n1}$, —$C(O)OR_{n1}$ and —$C(O)NR_{q1}R_{r1}$, wherein any $(C_1\text{-}C_6)$alkyl of $Z^1$ is optionally substituted with one or more (e.g. 1, 2, 3, 4, 5 or 6) halogen;

each $R_{n1}$ is independently selected from H and $(C_1\text{-}C_6)$alkyl, wherein any $(C_1\text{-}C_6)$alkyl of $R_{n1}$ is optionally substituted with one or more (e.g. 1, 2, 3, 4, 5 or 6) halogen;

each $R_{p1}$ is independently $(C_1\text{-}C_6)$alkyl; and $R_{q1}$ and $R_{r1}$ are each independently selected from H and $(C_1\text{-}C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine;

or a salt thereof.

2. The compound of claim 1 wherein:

each $R^1$ is independently H, $(C_1\text{-}C_6)$alkyl, $(C_3\text{-}C_7)$carbocycle or $R_aC(=O)$—, and the two $R^4$ groups together form a —$(C_3\text{-}C_8)$alkyl-group, a —$(C_2\text{-}C_6)$alkyl-Y—$(C_2\text{-}C_6)$alkyl-group or a —$(C_1\text{-}C_6)$alkyl-Y'—$(C_1\text{-}C_6)$alkyl-group; or each $R^4$ is independently H, $(C_1\text{-}C_6)$alkyl, $(C_3\text{-}C_7)$carbocycle or $R_aC(=O)$—, and the two $R^1$ groups together form a —$(C_3\text{-}C_8)$alkyl-group, a —$(C_2\text{-}C_6)$alkyl-Y—$(C_2\text{-}C_6)$alkyl-group or a —$(C_1\text{-}C_6)$alkyl-Y'—$(C_1\text{-}C_6)$alkyl-group; or the two $R^4$ groups together form a —$(C_3\text{-}C_8)$alkyl-group, a —$(C_2\text{-}C_6)$alkyl-Y—$(C_2\text{-}C_6)$alkyl group or a —$(C_1\text{-}C_6)$alkyl-Y'—$(C_1\text{-}C_6)$alkyl-group and the two $R^1$ groups together form a —$(C_3\text{-}C_8)$alkyl-group, a —$(C_2\text{-}C_6)$alkyl-Y—$(C_2\text{-}C_6)$alkyl-group or a —$(C_1\text{-}C_6)$alkyl-Y'—$(C_1\text{-}C_6)$alkyl-group;

the dashed bonds labeled "a" are absent and the dashed bonds labeled "b" are double bonds; or all the dashed bonds are single bonds;

$R^2$ is H, $(C_1\text{-}C_6)$alkyl or aryl, wherein aryl is optionally substituted with one or more $Z^1$ groups;

$R^3$ is H, $(C_1\text{-}C_6)$alkyl or aryl, wherein aryl is optionally substituted with one or more $Z^1$ groups;

Y is O, S, NH, P, P(=O) or POH;

Y' is $Si(R_b)_2$ or —$Si(R_b)_2$—O—$Si(R_b)_2$—;

each $R_a$ is independently $(C_1\text{-}C_6)$alkyl, $(C_3\text{-}C_7)$carbocycle or aryl, wherein aryl is optionally substituted with one or more $Z^1$ groups;

each $R_b$ is independently $(C_1\text{-}C_6)$alkyl, $(C_3\text{-}C_7)$carbocycle or aryl, wherein aryl is optionally substituted with one or more $Z^1$ groups; and each $Z^1$ is independently selected from $(C_1\text{-}C_6)$alkyl, halogen, —CN, —$OR_{n1}$, —$NR_{q1}R_{r1}$, —$NR_{n1}COR_{p1}$, —$NR_{n1}CO_2R_{p1}$, $NO_2$, —$C(O)R_{n1}$, —$C(O)OR_{n1}$ and —$C(O)NR_{q1}R_{r1}$, wherein any $(C_1\text{-}C_6)$alkyl of $Z^1$ is optionally substituted with one or more (e.g. 1, 2, 3, 4, 5 or 6) halogen;

each $R_{p1}$ is independently selected from H and $(C_1\text{-}C_6)$alkyl, wherein any $(C_1\text{-}C_6)$alkyl of $R_{n1}$ is optionally substituted with one or more (e.g. 1, 2, 3, 4, 5 or 6) halogen;

each $R_{p1}$ is independently $(C_1\text{-}C_6)$alkyl; and $R_{q1}$ and $R_{r1}$ are each independently selected from H and $(C_1\text{-}C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine.

3. The compound of claim 1 which is a compound of formula Ia:

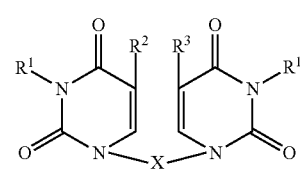

Ia wherein X is a —$(C_3\text{-}C_8)$alkyl-group or a —$(C_2\text{-}C_6)$alkyl-Y—$(C_2\text{-}C_6)$alkyl-group or a —$(C_1\text{-}C_6)$alkyl-Y'—$(C_1\text{-}C_6)$alkyl-group; or a salt thereof.

4. The compound of claim 1 which is a compound of formula Ib:

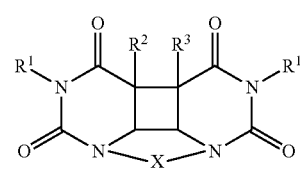

Ib wherein X is a —$(C_3\text{-}C_8)$alkyl-group or a —$(C_2\text{-}C_6)$alkyl-Y—$(C_2\text{-}C_6)$alkyl-group or a —$(C_1\text{-}C_6)$alkyl-Y'—$(C_1\text{-}C_6)$alkyl-group; or a salt thereof.

5. The compound of claim 1 wherein each $R^1$ is independently H or $(C_1\text{-}C_6)$alkyl, and the two $R^4$ groups together form a —$(C_2\text{-}C_6)$alkyl-Y—$(C_2\text{-}C_6)$alkyl- or a —$(C_1\text{-}C_6)$alkyl-Y'—$(C_1\text{-}C_6)$alkyl-group.

6. The compound of claim 3 wherein X is —$(C_2\text{-}C_6)$alkyl-Y—$(C_2\text{-}C_6)$alkyl-.

7. The compound of claim 1 wherein Y is NH.

8. The compound of claim 1 wherein $R^1$ is H.

9. The compound of claim 1 wherein $R^2$ and $R^3$ are each independently $(C_1\text{-}C_6)$alkyl.

10. The compound of claim 1 selected from:

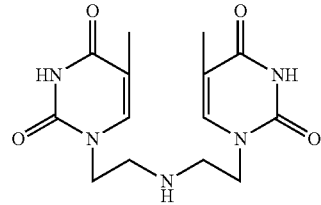

and

-continued

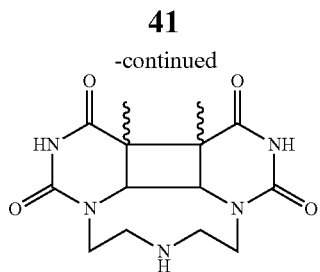

and salts thereof.

11. The compound of claim 1 which is not:

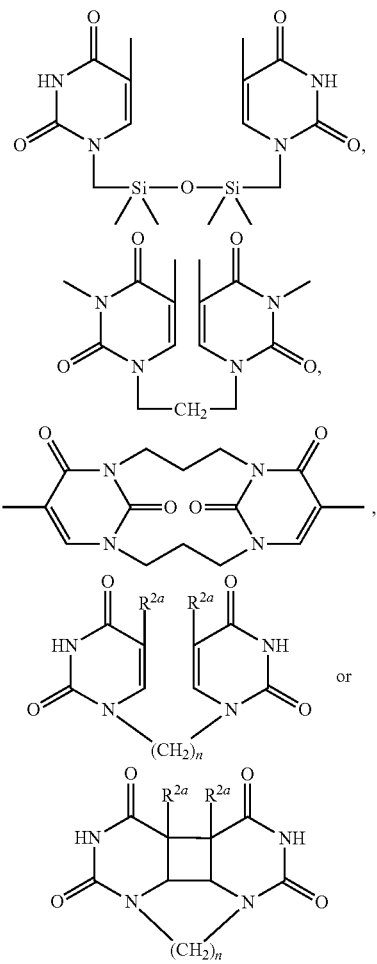

wherein each $R^{2a}$ is methyl or each $R^{2a}$ is ethyl; and n is 3-6.

12. The compound of claim 1 selected from:

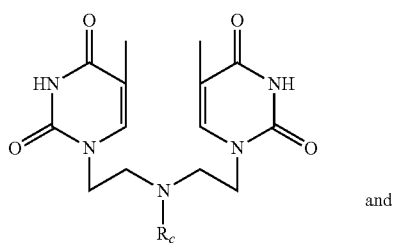

and

-continued

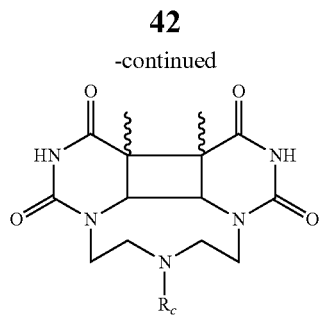

and salts thereof.

13. The compound of claim 12 wherein $R_c$ is selected from butanoyl, hexadecanoyl, octadecanoyl, benzoyl, 3-phenyl-prop-2-enoyl, 3-(4-methoxyphenyl)prop-2-enoyl, 3-carboxy-3-hydroxypropanoyl, 2-(N-acetylamino)-3-mercaptopropanoyl, 4-(4-methoxy-3-sulfobenzoyl)benzoyl, 4-(3-(4-methoxyphenyl)-1,3-dioxopropyl)benzoyl, and

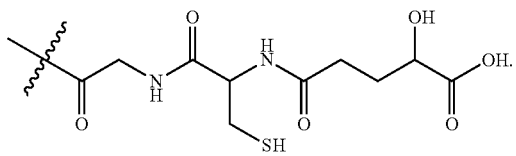 [SMILES: *C(=O)CNC(=O)C(CS)NC(=O)CCC(O)C(=O)O]

14. The compound of claim 1 which is selected from:

24a

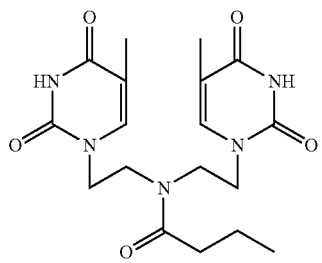

24b

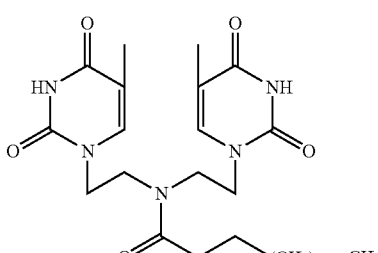

24c

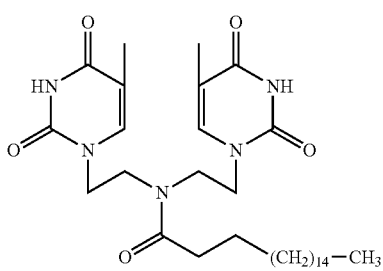

-continued
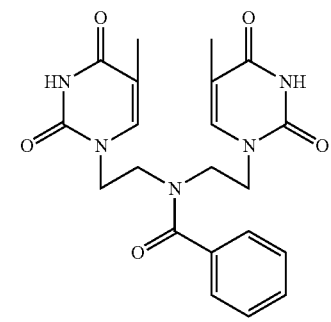
24d
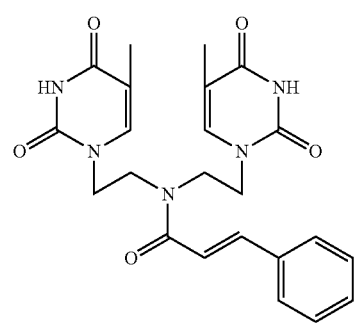
24e
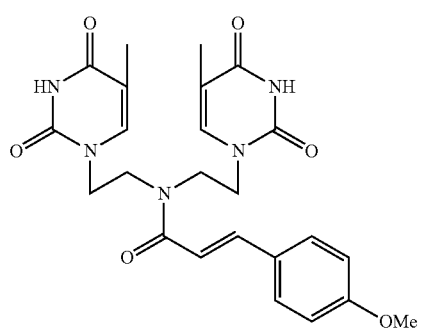
24f
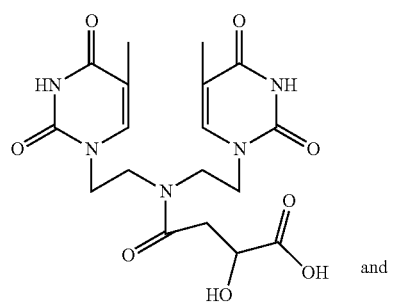
28
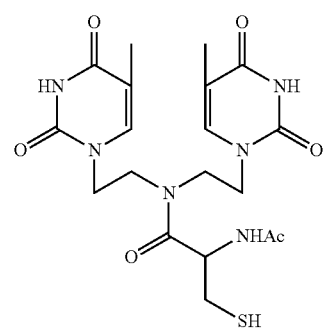
and
32
and salts thereof.
15. The compound of claim 1 which is selected from:
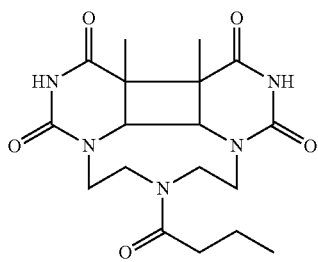
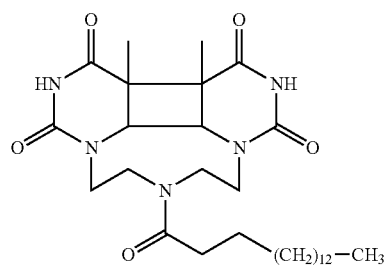
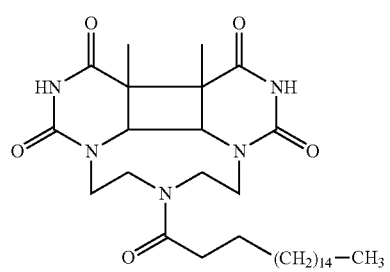
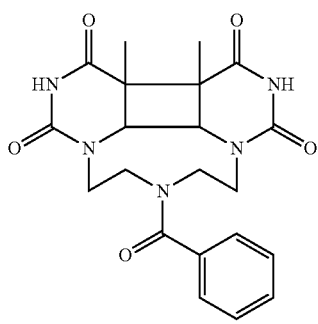
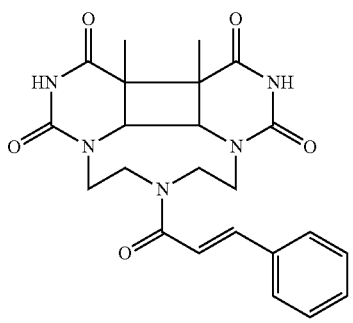

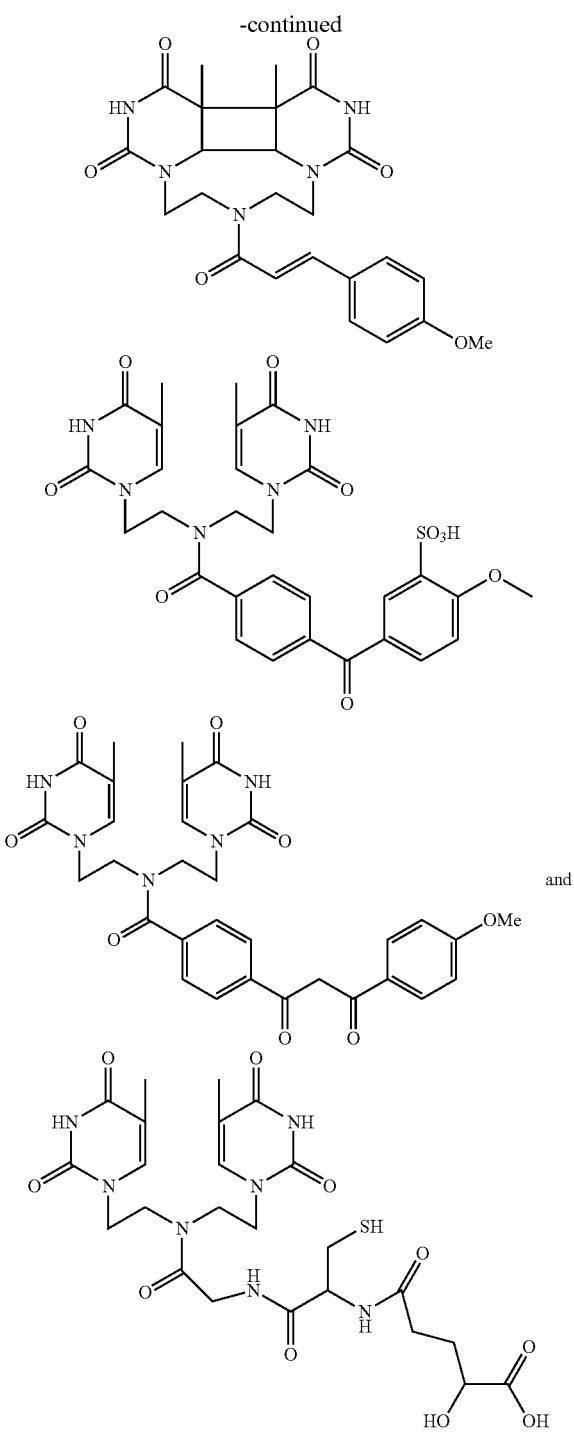

and salts thereof.

16. A composition comprising a compound of claim 1 or a pharmaceutically acceptable salt thereof, and a pharmaceutically acceptable carrier.

17. A composition comprising a mixture of two or more compounds as described in claim 1 or pharmaceutically acceptable salts thereof, and a pharmaceutically acceptable carrier.

18. The composition of claim 17 wherein at least one compound is a compound of formula Ia or pharmaceutically acceptable salt thereof and at least one compound is a compound of formula Ib or pharmaceutically acceptable salt thereof:

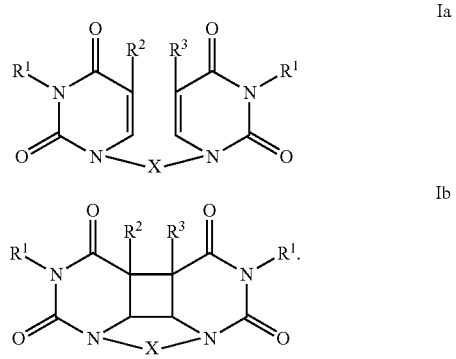

19. A method of protecting mammal skin from photo-damage comprising contacting the skin with one or more compounds as described in claim 1 or pharmaceutically acceptable salts thereof.

20. A method of protecting DNA in mammal skin from photo-damage comprising contacting the skin with one or more compounds as described in claim 1 or pharmaceutically acceptable salts thereof.

21. A method of repairing photo-damage in a mammal skin comprising contacting the skin with one or more compounds as described in claim 1 or pharmaceutically acceptable salts thereof.

22. A method of stimulating DNA repair in a mammal skin comprising contacting the skin with one or more compounds as described in claim 1 pharmaceutically acceptable salts thereof.

23. A method of reducing the likelihood of contracting skin cancer in a mammal comprising contacting the skin with one or more compounds as described in claim 1 or pharmaceutically acceptable salts thereof.

24. The method of claim 23 wherein the skin cancer is basal cell carcinoma or squamous cell carcinoma.

25. A method of reversing the signs of skin aging in a mammal comprising contacting the skin with one or more compounds as described in claim 1 or pharmaceutically acceptable salts thereof.

26. A method of treating xeroderma pigmentosum in a mammal comprising contacting the skin with one or more compounds as described in or pharmaceutically acceptable salts thereof.

27. The method of claim 26 wherein the mammal is being treated with an immunosuppressant agent.

28. The method of claim 27 wherein the immunosuppressant agent is a transplant rejection agent or an anti-HIV agent.

29. A method of treating ionizing radiation damage in a mammal comprising treating the mammal with one or more compounds as described in claim 1 or pharmaceutically acceptable salts thereof.

* * * * *